US008645106B2

(12) United States Patent
Kisanuki et al.

(10) Patent No.: US 8,645,106 B2
(45) Date of Patent: Feb. 4, 2014

(54) METHOD OF DETERMINING SHAPE OF ARTIFICIAL CEMENTLESS HIP PROSTHESIS STEM

(75) Inventors: Kojima Kisanuki, Kakamigahara (JP); Nobuhiko Sugano, Suita (JP)

(73) Assignee: Kabushiki Kaisha B.I. TEC, Gifu (JP)

( * ) Notice: Subject to any disclaimer, the term of this patent is extended or adjusted under 35 U.S.C. 154(b) by 704 days.

(21) Appl. No.: 12/935,448

(22) PCT Filed: Mar. 31, 2009

(86) PCT No.: PCT/JP2009/001515
§ 371 (c)(1),
(2), (4) Date: Oct. 18, 2010

(87) PCT Pub. No.: WO2009/122731
PCT Pub. Date: Oct. 8, 2009

(65) Prior Publication Data
US 2011/0035192 A1    Feb. 10, 2011

(30) Foreign Application Priority Data
Mar. 31, 2008    (JP) ................................. 2008-094367

(51) Int. Cl.
*G06F 17/50*    (2006.01)
(52) U.S. Cl.
USPC .......................................................... 703/1
(58) Field of Classification Search
CPC ...................................................... G06F 17/50

USPC .............................. 703/1; 623/22.11; 700/117
See application file for complete search history.

(56) References Cited

U.S. PATENT DOCUMENTS 5,152,795 A * 10/1992 Sioshansi et al. ............. 424/423
2005/0065628 A1 * 3/2005 Roose ........................... 700/117

FOREIGN PATENT DOCUMENTS

JP    200137792 A1    2/2001
WO    2005034818 A1    4/2005

* cited by examiner

Primary Examiner — Kamini S. Shah
Assistant Examiner — Luke Osborne
(74) Attorney, Agent, or Firm — William J. Sapone; Ware Fressola; Maguire & Barber LLP

(57) ABSTRACT

A custom-made stem has a shape displaying good fit and fill, reflecting personal characteristics of a femur obtained by computer calculation. A model is made from the femur which does not need much time to calculate in spite of the fact that it complies with the characteristic of shape of the femur, particularly with the personal difference in the curvature thereof, which usually complicates the calculation. Several models are made which can be implanted in a deep hollow by calculating in a reverse course how the stem is pulled out of the deep hollow, to display reliable models to a surgeon. By determining the movement peculiar to the stem of a particular patient, an improved stem is made in a short time which meets the needs of the surgeon. The stem, which is custom-made, can be confirmed beforehand that it agrees with the femur of the patient.

23 Claims, 29 Drawing Sheets

ମETHOD OF DETERMINING SHAPE OF ARTIFICIAL CEMENTLESS HIP PROSTHESIS STEM

TECHNICAL FIELD

The present invention relates to a method of determining shape of artificial cement-less hip prosthesis stem, more particularly, to a method of determining the shape of hip prosthesis stem which supports a spherical head substituting for a damaged caput and transmits the load from a pelvis to a femur, so that several examples of the shape of stems to be usable in the surgical operation and illustrations of the process manner of implanting stem into the deep hollow can be shown to the surgeon before the actual operation. With the tendency of the transition in stem's position and posture grasped, the preferable stem can be easily selected in consideration of his own ability and the present condition of the femur and even the rates of Fit and Fill. Moreover, the examples of stem allow the surgeon to think of new improved stems, making it possible to show a new variation reflecting his idea in a short time, thereby, the movement of the stem goes well according to his plans from the beginning of inserting into the deep hollow to the end, and what is more, the visible image of the transition in the movement thereof, may release him from fear and suspicion in the operation.

BACKGROUND ART

A femur 1 consists of, as shown in FIG. 26(a), a caput 61, a neck part 62, a greater trochanter 42, and a lesser trochanter (not shown), in the diaphysis 63 thereof a medullary cavity 6 is formed. The surface layer of the femur 1 is cortical bone 66, and in the epiphysis 67 spongiosa 68 supports the cortical bone 66 from the inside by means of back-up effect. The break of the caput 61 engaged with an acetabulum, not shown, of pelvis to form spherical joint, due to a traffic accident or the like as shown in FIG. 26 (b) or deteriorating the femur due to osteoporosis, make it nearly impossible for the femur 1 to support the load 69 transmitted from the pelvis.

It is often possible to recover the function of transmitting the load, depending on the remaining shape of the femur 1 and the stiffness of the cortical bone 66. In order to recover the function, a spherical head 70 working as a caput is fixed to the femur 1 through a stem 71, as shown in FIG. 26(c). Before inserting the stem into the femur, the cortical bone 66 in the epiphysis 67 is generally cut off, as shown by the dot-dash-line in FIG. 26(b). By using a stem 71 and a rasp 46 shown in FIG. 27, the spongiosa 68 is excised so as to form a deep hollow 4. The stem 71 consists of a neck 72 for supporting a spherical head 70, a nose 73 for working as a guide while being inserted into the deep hollow 4 and for keeping the posture thereof after being fixed in the femur, and a body 32 for transmitting the load by shearing stress occurring at the interface between the surface of the stem and the surface of the deep hollow.

So far there are two methods of fixing the stem 71 in the deep hollow 4; a method of uniting the stem with the deep hollow by cement, the other method of filling the interface not with cement but with spongiosa gradually grown on the surface of the deep hollow. Although cement turns into a solid in a short period of time, un-reacted monomer may lixiviate therefrom, often causing the pulmonary embolism. Although Bone-Growth of spongiosa is quite harmless to human bodies, it needs a long hospitalization, for it requires much time to unite them. From that point of view, recently the research and the development of artificial cement-less hip prosthesis stem has been prospering on the grounds that the stem can be easily removed from a femur when replacing the stem in the future and that it will not chemically deteriorate.

The rasp mentioned above is driven into the femur 1 from the epiphysis 67 toward the diaphysis 63, gradually moved up and down to excise the spongiosa 68, thus the deep hollow is formed. In the case of fixing by using cement, an oversize rasp than the stem 71 is used for forming the deep hollow 4, but in the case of fixing by Bone-Growth which makes the stem unite to the femur, an undersize rasp than the stem is used for forming the deep hollow. In any case, the rasp is approximately similar to the stem in shape, but the curvature of the femur 1 and the thickness of the remaining cortical bone 66 differ with patients, stems of ordinary shape and size are often unavailable.

In the case of fixing by using cement, it is not always necessary for a rasp to be closely similar to a stem in shape, because a space is given beforehand for filling cement in the deep hollow 4. Examining the state of wall of the deep hollow in advance from the data of three-dimensional CT graphics of the femur in order to successfully form the deep hollow, may avoid damaging the cortical bone 66 while forming the deep hollow. The stem 71 having little bend as shown in FIG. 26(c) can be inserted straight into the deep hollow previously filled with cement like the arrow 85, which promotes the standardizing the shape and the size of the stem, the handling simply and easily to insert the stem, ready-made of stems, and reducing in doctor's fee, in spite of the drawback that un-reacted monomer may lixiviate from the cement.

In the case of fixing by Bone-Growth, however, a stem and a rasp need to be closely similar in shape and size. The CT graphics data 75 shown in FIG. 28(a) and MRI data are obtained from the femur 1 to have prosthesis, which are peculiar to the patient, by means of non-destroying section photography equipment. The three dimensional graphics 76 shown in FIG. 28 (b) is made from these data, the threshold value of bone density 77, that is Gray Scale, shown in FIG. 28(c) is applied to the graphics, which is necessary for the patient's femur to form the deep hollow. The threshold value determined by the surgeon will detect the limitary thickness of the cortical bone on each part of the femur, the inner surface obtained by smoothing the inside of the bony tissue having the limitary thickness, will assign the suitable shape and the size to the deep hollow.

The idea has already known of custom-making the stem to be implanted in the deep hollow made as mentioned above. But since the stem is a metal product made of titanium alloy or the like which does not usually cause any chemical change and the stem is manufactured by casting, it will cost a great deal to get the stem fitting the patient, including the cost of a metallic mold which has to be made individually for each patient. In JP2001-33792A1, for instance, it is disclosed that a rough part for forming a deep hollow is obtained from many CT graphics of a femur so as to prepare several standards of stem which fit the part. In WO2005/034818, a method is disclosed of making a mold for forming a stem automatically by NC-machine receiving the numerical data indicating the shape of stem, which are equal to a shape of deep hollow computed from CT graphics of the femur to take a surgery according to the surgeon's opinion.

However, designing stem and manufacturing metallic mold by computer have not been realized yet. The actual situation of the process of operation is as follows; the staffs in charge of the operation take CT graphics of the femur and send them to a manufacturer of stem. The manufacturer which has thirty kinds, for the present, of stems of typical shape and size, and the rasps corresponding to the stems on hand, selects five or so stems and rasps nearly agreed with the CT data and sends them to the staffs. The surgeon selects one rasp from them and excises the femur with it so as to find a proper use of it, or may try out other rasps if necessary. While using the rasps, he may find the best rasp which is easy for handling or suitable for the patient to complete the deep hollow.

The stem is used which corresponds to the rasp last-used, the surgeon inserts this stem so as to move along the wall of the deep hollow. Since the deep hollow is slightly smaller than the stem, the stem can be arranged at the desired position by his last pushing or tapping. At this point, some of the stem's surface tightly contact the spongiosa remaining on the surface of the deep hollow, the stem settles in the state that the stem sticks to the femur. The staff in charge decide to purchase the rasp and the stem, sending back other rasps and stems to the manufacturer. The surgeon is obliged to try forming the hollow by using only a few rasps which have been sent from the manufacturer, resulting in that the surgeon cannot select the favorable rasp until he tries all of the rasps.

More particularly, although the surgeon may tell the manufacturer his requirements on the shape and the size of the deep hollow drawn from the CT graphics, the rasps given by the manufacturer are just selected among the standards, accordingly the shape and the size thereof may not always meet with his requirements. Even if a transition in the posture of the rasp is shown by the manufacturer from the beginning of excising the hollow to the end, this is still at the level of a rough suggestion. The surgeon has to start the operation with no opportunity to practice handling the rasp, and does not have much reliance on the rasp throughout the operation. What the surgeon can do is only to do his best in using the rasp sent from the manufacturer, so that it is impossible for him not only to realize his ideal in handling the rasp and the stem in response to the femur of the patient, but to obtain the rasp and the stem to which he introduces his ability and his peculiar way in handling them.

A stem 71 which can be inserted linearly as shown in FIG. 26 (*c*), is necessarily thinner than the femur 1. A stem without a bend such as the stem 71 has the advantage of being easy to mold, however, in the case that a stem is fixed by Bone-Growth, the stem is liable to be unstable in its posture and to come off from the femur, for the stem is supported by spongiosa 68 whose supporting and fixing properties are not sufficient. Incidentally, a stem made of fiber reinforced plastics is obtainable by using a ceramics mold, so that it should be manufactured at a low price in spite of the fact that it is custom-made, moreover, it is easy to make the stem having a bend in response to the femur of the patient, therefore, it is expected that the stem will be available which fits his femur best.

It is ideal for the stem to be settled in the femur, however, the question is how to successfully bring the stem into the position and the posture. If any part of the stem hits the deep hollow on the surface during the inserting of the stem, further inserting thereof will break the deep hollow, therefore the problem is how to obtain the necessary and sufficient space to move the stem without making the deep hollow oversize than it needs. There are two solutions to the problem, one is that the shape and the size of the stem are determined beforehand and then the suitable shape and size of the deep hollow is obtained which enables the stem to be inserted, and the other is obtained vice versa. In any case, it depends on whether the course can be specified or not that the stem is inserted so as not to hit the inside of the bony tissue having the limitary thickness.

That the stem can be implanted in the fixed preferable position of the deep hollow means that the stem can be removed from the deep hollow. Consequently, it is effective to find out the course that the stem settled in the deep hollow is successfully removed from the deep hollow. As illustrated in FIG. 29, the shadowed stem 80 in fixed position is lifted by one step as shown by the arrow 81, successively lifted step by step through the position of the stem 82, removed from the deep hollow at the position of the stem 83.

Even in the first step, at least four kinds of positions and postures of the stem 84 are shown in Figure, where the stem is lifted in the deep hollow 4 by a height of the arrow 81. It goes without saying that there are boundless positions and postures theoretically in spite of the fact that the stem is restricted to move in the deep hollow. Moving up the stem to the next step of the arrow 85, makes the number of postures of the stem multiply boundlessly every posture of the last step, not shown. Furthermore, much more numbers of the positions and postures of the stem at the second step have to be assumed than those of the first step, thus there are limitless courses to reach the stem 83 of the last step. Enormous calculations will be needed before preparing for detecting the preferable course, resulting in mere waste of time and money. It is absolutely impossible to find out the best combination of the stem and the deep hollow for taking the positions and the postures to be adopted from the boundless combinations, with grasping the rates of Fit and Fill of each stem.

This problem is caused by that the deep hollow has extra room for the stem to move therein. However, if the deep hollow is too tight to restrict the movement of the stem, the stem cannot be lifted from the starting position or perhaps on the way, making it impossible to calculate. This is because the stem whose curvature varies with its part cannot be removed from the deep hollow when the shape and the size of the deep hollow are the same or almost the same as those of the stem. In determining the shape of the stem which can be inserted into the deep hollow, making the deep hollow beforehand to be oversize than the stem causes the limitless kinds of postures of the stem, which makes it impossible to calculate, as mentioned above.

Patent Document 1 JP2001-33792A1
Patent Document 2 WO2005/034818

DISCLOSURE OF INVENTION

Purpose of Invention

The first object of the present invention relating to an artificial cement-less hip prosthesis stem is both to make calculating itself possible and to shorten the time for calculating by specifying not only the shape and size of stem and deep hollow but the position and posture of stem, which satisfy several assumed curvatures acceptable to the femur to take a surgical operation, while being inserted into the deep hollow. The second object is to show the shape and size of each stem and deep hollow, the position and posture of the stem, and furthermore the rates of Fit and Fill of the stem to the deep hollow in each case of stems having several reliable curvatures. The third object is to enable the surgeon to efficiently determine the stem to be applied by obtaining the course of inserting the stem into the femur to take surgery treatment from these data mentioned above, and by showing variations introducing demands of the surgeon as well. The fourth object is to prepare for the operation so that the surgeon can confidently perform the surgical operation without any uneasiness by letting him know beforehand the transition in the position and posture of the stem to be implanted into the deep hollow by means of making a series of pictures of the adopted stem being implanted into the femur and visual confirmation thereof and giving an demonstration by using models and so on.

SUMMARY OF INVENTION

The present invention is applied to a method of determining the shape of the artificial cement-less hip prosthesis stem, which is implanted into the deep hollow extending from the epiphysis of the femur to the diaphysis, so as to be gradually united with the femur by Bone-Growth, the method comprises as follows;

detecting the limitary thickness of the bony tissue of each part of the femur to have prosthesis, which is necessary for forming the wall of the deep hollow, by applying threshold value of bone density to the three dimensional graphics data based on CT graphics data and MRI data obtained from the femur, calculating not only the shape of the imaginary three dimensional deep hollow extending to the medullary cavity, which is formed inside the bony tissue, but the coordinates of crotch side line and counter-crotch side lines for regulating the shape of lateral section of the deep hollow, and the coordinates of anterior side line and posterior side line for regulating the shape of section perpendicular to the lateral section of the deep hollow;

calculating not only the shape of the epiphysis opening of the imaginary three dimensional deep hollow and the position of the center of figure of the shape, from the position and the angle of the epiphysis opening determined on the basis of the reference line given beforehand so as to be parallel to the longitudinal direction of the femur, but the shape of the diaphysis opening of the imaginary three dimensional deep hollow and the position of the center of figure of the shape, from the length of the stem to be applied to the femur and the angle of the diaphysis opening, calculating the reference arc on the plane including the crotch side line and counter-crotch side line which passes through the center of figure of the epiphysis opening mentioned above, the center of figure of the diaphysis opening, and the reference point in the lateral direction, which lies halfway between these two centers of figure, and from which the distance to said crotch side line is approximately equal to the distance to the counter-crotch side line;

obtaining the pattern of the provisional deep hollow on the plane including the crotch and counter-crotch side lines, which is formed inside said imaginary three dimensional deep hollow surrounded by a small arc on the plane including the crotch and counter-crotch side lines which is concentric with the reference arc on the plane including the crotch and counter-crotch side lines and has a radius which is shorter than the radius of the reference arc and longer than the distance to the end point of epiphysis lying on said crotch side line, a large arc on the plane including the crotch and counter-crotch side lines which is concentric with said reference arc and has a radius which is longer than the radius of said reference arc and shorter than the distance to the end point of epiphysis lying on said counter-crotch side line, the crotch side line which is from the terminal point of the small arc where said small arc intersects the crotch side line to the end point of diaphysis lying on the crotch side line, and the counter-crotch side line which is from the terminal point of the large arc where said large arc intersects the counter-crotch side line to the end point of diaphysis lying on the counter-crotch side line;

calculating the reference arc on the plane including the anterior and posterior side lines which passes through the center of figure of the epiphysis opening mentioned above, the center of figure of the diaphysis opening, and the reference point in the direction perpendicular to the lateral direction, which lies halfway between these two centers of the figure, and from which the distance to said anterior side line is approximately equal to the distance to the posterior side line;

obtaining the pattern of the provisional deep hollow on the plane including the anterior and posterior side lines, which is formed inside said imaginary three dimensional deep hollow surrounded by a small arc on the plane including the anterior and posterior side lines which is concentric with the reference arc on the plane including the anterior and posterior side lines and has a radius which is shorter than the radius of the reference arc and longer than the distance to the end point of epiphysis lying on said anterior side line, a large arc on the plane including the anterior and posterior side lines which is concentric with said reference arc and has a radius which is longer than the radius of said reference arc and shorter than the distance to the end point of epiphysis lying on said posterior side line, the anterior side line which is from the terminal point of the small arc where said small arc intersects the anterior side line to the end point of diaphysis lying on the anterior side line, and the posterior side line which is from the terminal point of the large arc where said large arc intersects the posterior side line to the end point of diaphysis on the posterior side line;

making the provisional three dimensional reference stem containing the reference arc on the plane including the crotch and counter-crotch side lines and the reference arc on the plane including the anterior and posterior side lines, which consists of a body surrounded by four side planes formed by arranging said patterns of provisional deep hollow on the plane including the crotch and counter-crotch side lines on the anterior side line and the posterior side line respectively so as to face each other and said patterns of provisional deep hollows on the plane including the anterior and posterior side lines on the crotch side line and the counter-crotch side line respectively so as to face each other, and a quasi-circular cylinder having the same shape as said imaginary three dimensional deep hollow corresponding to the region from each terminal point of the small arc and the large arc of the body surrounded by four planes to the diaphysis opening;

making the provisional three dimensional reference deep hollow which has the same shape as said provisional three dimensional reference stem, in order to calculate the position and the posture of the provisional three dimensional reference stem on each step that the stem is gradually pulled out of the deep hollow, obtaining the residual portion of provisional three dimensional reference deep hollow whose diaphysis portion is removed, where the deep hollow does not overlap the stem every step, with calculating the center of gravity and the principal axes of inertial thereof, and obtaining the residual portion of provisional three dimensional reference stem whose epiphysis portion is removed, where the stem does not overlap the deep hollow every step, with calculating the center of gravity and the principal axes of inertial thereof as well, shifting the center of gravity of the residual portion of the provisional three dimensional reference stem to the principal axes of the residual portion of the deep hollow in the direction of pulling out the stem on the condition that the posture of the stem is kept in the step, rotating the residual portion of provisional three dimensional reference stem around the center of gravity shifted in the last step so as to coincide the principal axes of inertial of the residual portion of provisional three dimensional reference stem in the direction of pulling out the stem with the principal axes of inertial of the residual portion of provisional three dimensional reference deep hollow in the direction of pulling out the stem, calculating the positions that the end points of diaphysis lying on the crotch side line and the anterior side line of the residual portion of provisional three dimensional reference stem, and the end points of diaphysis lying on the counter-crotch side line and the posterior side line occupy every step;

making an imaginary three dimensional stem which has the same shape as said imaginary three dimensional deep hollow, moving the imaginary three dimensional stem in the imaginary three dimensional deep hollow by applying the transitional values of said occupied positions to the imaginary stem, calculating the interference portions where the imaginary three dimensional stem is disturbed to move in the imaginary three dimensional deep hollow while the stem is pulled out of the deep hollow and putting them in storage;

calculating the outer surface of shape of the imaginary three dimensional stem whose interference portions are entirely removed on the basis of the data in storage, obtaining the reference stem whose final shape is inscribed to the supposed inner surface of shape for the purpose of by smoothing the outer surface of shape of the imaginary three dimensional stem, taking an alternative reference point in the lateral direction on the region between a straight segment from the center of figure of the epiphysis opening to the center of figure of the diaphysis opening and said reference point in the lateral direction, taking an alternative reference point in the direction perpendicular to the lateral direction on the region between said straight segment and said reference point in the direction perpendicular to the lateral direction as well, regarding the alternative reference point in the lateral direction as the reference point in the lateral direction, and the alternative reference point in the direction perpendicular to the lateral direction as the reference point in the direction perpendicular to the lateral direction, obtaining the alternative provisional three dimensional reference stem having the alternative reference arc on the plane including the crotch and counter-crotch side lines whose curvature is different from that of the reference arc on the plane including the crotch and counter-crotch side lines and the alternative reference arc on the plane including the anterior and posterior side lines whose curvature is different from that of the reference arc on the plane including the anterior and posterior side lines, calculating said occupied positions every step, obtaining the final shape of the alternative stem instead of said reference stem by following the procedure for calculating the interference portions of the stem where the imaginary three dimensional stem is disturbed to move in the imaginary three dimensional deep hollow by using the occupied position, and for putting the data in storage, and computing the data on the positions and the postures of the reference stem and the alternative stem which have said final shape while putting these stems gradually into said imaginary three dimensional deep hollow, i.e., by taking the reverse steps of the series of steps mentioned above.

In the latter half of the series of steps that the provisional three dimensional reference stem is gradually pulled out of the provisional three dimensional reference deep hollow, moving the center of gravity of said residual portion of the provisional three dimensional reference stem along the line from said center of gravity of the residual portion of the provisional three dimensional reference stem to said center of figure of the epiphysis opening of said imaginary three dimensional deep hollow on the condition that the posture of the stem of every step is kept, calculating the occupied positions of the end points of diaphysis lying on the crotch side line and the anterior side line of the residual portion of the provisional three dimensional reference stem and of the end points of diaphysis lying on the counter-crotch side line and the posterior side line.

The radius of said small arc on the plane including the crotch and counter-crotch side lines is equal to the radius of the pseudo-arc regarding as the crotch side line which passes through the end point of diaphysis and the end point of epiphysis lying on the crotch side line of said imaginary three dimensional deep hollow, and the point most protruded in the lateral direction on the crotch side line, where the line parallel to the straight line passing through these two end points contacts the crotch side line, and the radius of said small arc on the plane including the anterior and posterior side lines is equal to the radius of the pseudo-arc regarding as anterior side line which passes through the end point of diaphysis and the end point of epiphysis lying on the anterior side line of said imaginary three dimensional deep hollow, and the point most protruded in the direction perpendicular to the lateral direction on the anterior side line, where the line parallel to the straight line passing through these two end points contacts the anterior side line.

The radius of said large arc on the plane including the crotch and counter-crotch side lines has the length equal to the addition of the difference between the radius of the reference arc on the plane including the crotch and counter-crotch side lines passing through the reference point in the lateral direction and the radius of said small arc on the plane including the crotch and counter-crotch side lines to the radius of the reference arc on the plane including the crotch and counter-crotch side lines, and the radius of said large arc on the plane including the anterior and posterior side lines has the length equal to the addition of the difference between the radius of the reference arc on the plane including the anterior and posterior side line passing through the reference point in the direction perpendicular to the lateral direction and the radius of said small circular arc including the anterior and posterior side line to the radius of the reference arc on the plane including the anterior and posterior side lines.

Said reference point in the lateral direction is the midpoint of the line from the point most protruded in the lateral direction on the crotch side line to the cross point where the line passing through the center of said pseudo-arc regarding as the crotch side line and the point most protruded in the lateral direction on the crotch side line intersects the counter-crotch side line, said reference point in the direction perpendicular to the lateral direction is the midpoint of the line from the point most protruded in the direction perpendicular to the lateral direction on the anterior side line to the cross point where the line passing through the center of said pseudo-arc regarding as the anterior side line and the point most protruded in the direction perpendicular to the lateral direction on the anterior side line intersects the posterior side line.

The ratio of the distance from said straight segment to the alternative reference point in the lateral direction taken between said straight segment and said reference point in the lateral direction to the distance from the straight segment to said reference point in the lateral direction, is defined by bending ratio $\alpha$ on the plane along the lateral direction, and the ratio of the distance from the straight segment to the alternative reference point in the direction perpendicular to the lateral direction taken between said straight segment and said reference point in the direction perpendicular to the lateral direction to the distance from the straight segment to said reference point in the direction perpendicular to the lateral direction, is defined by bending ratio $\beta$ on the plane along the direction perpendicular to the lateral direction, case of α=0 and β=0
case of α=0.5 and β=0
case of α=1 and β=0
case of α=0 and β=0.5
case of α=0.5 and β=0.5
case of α=1 and β=0.5
case of α=0 and β=1
case of α=0.5 and β=1
case of α=1 and β=1 in all or some cases of above nine cases, the transitional values of the positions and the postures of the imaginary rasps, which are previously given the same shape and size as the reference stem and the alternative stem having said final shape, are calculated while the imaginary rasps are independently pushed into the imaginary three dimensional deep hollow step by step.

After obtaining said cases that the imaginary rasps are pushed into the imaginary three dimensional deep hollow, the bending ratio α on the plane along the lateral direction and the bending ratio β on the plane along the direction perpendicular to the lateral direction can be changed into the desired values of the surgeon, the final shape of the re-alternative stem corresponding to said reference stem is obtained by regarding a re-alternative reference point in the lateral direction obtained from the new ratio α as said reference point in the lateral direction, and by regarding re-alternative reference point in the direction perpendicular to the lateral direction obtained from the new ratio β as said reference point in the direction perpendicular to the lateral direction, the data on the positions and the postures of the re-alternative stem having the final shape of every step are computed while putting the re-alternative stem into said imaginary three dimensional deep hollow, i.e., by taking the reverse steps of the series of steps mentioned above, and the transitional values of the positions and the postures of the re-imaginary rasp having the same shape and the size as those of the re-alternative stem having the final shape are computed while putting the re-alternative rasp into the imaginary deep hollow step by step.

After putting said reference stem, the alternative stem and the re-alternative stem into said imaginary three dimensional deep hollow, the rates of Fit and Fill are calculated of every section of each stem along said reference line.

EFFECT OF INVENTION

According to the present invention, the pattern of provisional deep hollow on the plane including the crotch and counter-crotch side lines and the pattern of provisional deep hollow on the plane including the anterior and posterior side lines are obtained by substituting the imaginary three dimensional deep hollow whose cross section has regular curvature for the deep hollow formed in the femur to have a surgery, whose cross section has irregular curvature, thereby, the provisional three dimensional reference stem is obtained, which consist of a body formed by a body surrounded by four side planes, i.e., patterns mentioned above, and nose formed by the corresponding part of the patient's deep hollow, and the provisional three dimensional reference deep hollow having the same shape as the reference stem is also obtained to substitute for the imaginary three dimensional deep hollow. The calculation displaying the high accuracy of overlapping the provisional three dimensional reference stem on the provisional three dimensional reference deep hollow specifies the combination of the positions and postures of the reference stem by coinciding its principal axes of inertial with that of the reference deep hollow by one step while the stem is pulled out of the reference deep hollow to only one combination of them, realizing the calculating for designing the provisional three dimensional reference stem with such a specified curvature. The positions and the postures of the provisional three dimensional reference stem, which have already obtained by the calculation mentioned above, are applied to the imaginary three dimensional stem having the same shape as the imaginary three dimensional deep hollow to obtain the portions interfered with the imaginary three dimensional deep hollow while the stem is pulled out of the imaginary three dimensional deep hollow and to remove the interference portion from the reference stem, resulting in achieving the high rate of Fill at the body of the reference stem and the high rate of Fill at the nose, though the imaginary three dimensional deep hollow is used in the calculation instead of the actual deep hollow.

An alternative stem can be obtained, which takes the place of the reference stem, in the same way as the calculating mentioned above by applying another curvature to the provisional deep hollow on the plane including the crotch and counter-crotch side lines and the provisional deep hollow on the plane including the anterior and posterior side lines. Preparing several kinds of the alternative stems helps the surgeon to know the tendency of the transitional values of the positions and the postures of the stem in response to the various curvatures, so that the surgeon can select the stem being close to his plan of handling among them, thereby, the curvature of the stem to be used is selected quickly and easily. Visually learning the transitional values of the positions and the postures of the stem beforehand by means of steady pictures or a series of pictures thereof, making plastic models of the stem and the femur on the basis of the calculated data, help the surgeon to make sure the process of implanting the stem with the sense of touch before the surgical operation. The fact that the shape of the rasp is nearly the same as that of the stem will get rid of his uneasiness in handling the rasp, and the duration for the surgery may be shortened.

In the latter half of the series of steps in which the provisional three dimensional reference stem is gradually pulled out of the provisional three dimensional reference deep hollow, the center of gravity of the residual portion of the provisional three dimensional reference stem is moved along the line from the center of gravity of the residual portion of the provisional three dimensional reference stem to the center of figure of the epiphysis opening of the imaginary three dimensional deep hollow, by one step, on the condition that the posture of the stem of every step is kept. The imaginary three dimensional stem is moved in the imaginary three dimensional deep hollow by applying the transitional values of the occupied positions of the end points of diaphysis lying on the crotch side line and the anterior side line of the residual portion provisional three dimensional reference stem and of the occupied positions of the end points the diaphysis lying on the counter-crotch side line and the posterior side line to the imaginary three dimensional stem, so that the end of the imaginary three dimensional stem certainly passes through the center of figure of the epiphysis opening at the moment that the imaginary three dimensional stem is pulled out of the imaginary three dimensional deep hollow, accordingly the surgeon can confidently begin with placing a rasp at the center of the epiphysis opening to make a deep hollow.

The radius of the small arc on the plane including the crotch and counter-crotch side lines is equal to the radius of the pseudo-arc regarding as the crotch side line which passes through the end point of diaphysis and the end point of epiphysis lying on the crotch side line of the imaginary three dimensional deep hollow and the point most protruded in the lateral direction on the crotch side line, where the line parallel to the straight line passing through these two end points contacts the crotch side line. The radius of the small arc on the plane including the anterior and posterior side lines is equal to the radius of the pseudo-arc regarding as anterior side line which passes through the end point of diaphysis and the end point of epiphysis lying on the anterior side line of the imaginary three dimensional deep hollow, and the point most protruded in the direction perpendicular to the lateral direction on the anterior side line, where the line parallel to the straight line passing through these two end points contacts the anterior side line. Thus the curvatures can be maximized of the reference arc on the plane including the crotch and counter-crotch side lines and the reference arc on the plane including the anterior and posterior side lines, which means that it is not necessary to make reference arcs having curvatures exceeding these curvatures, so that the calculation which is for the part where the femur does not occupy can be eliminated beforehand from the calculating.

The radius of the large arc on the plane including the crotch and counter-crotch side lines is designed to have the length equal to the addition of the difference between the radius of the reference arc on the plane including the crotch and counter-crotch side lines passing through the reference point in the lateral direction and the radius of the small arc on the plane including the crotch and counter-crotch side lines to the radius of the reference arc on the plane including the crotch and counter-crotch side lines. And the radius of the large arc on the plane including the anterior and posterior side lines is designed to have the length equal to the addition of the difference between the radius of the reference arc on the plane including the anterior and posterior side line passing through the reference point in the direction perpendicular to the lateral direction and the radius of the small arc on the plane including the anterior and posterior side line to the radius of the reference arc on the plane including the anterior and posterior side lines. Thus, in calculating the transitional values of the positions and the postures of the provisional three dimensional reference stem, the calculation which is for the space in greater trochanter and lesser trochanter where the stem does not occupy can be eliminated beforehand from the calculating process of the provisional three dimensional reference stem.

The reference point in the lateral direction is the midpoint of the line from the point most protruded in the lateral direction on the crotch side line to the cross point where the line passing through the center of the pseudo-arc regarding as the crotch side line and the point most protruded in the lateral direction on the crotch side line intersects the counter-crotch side line, and the reference point in the direction perpendicular to the lateral direction is the midpoint of the line from the point most protruded in the direction perpendicular to the lateral direction on the anterior side line to the cross point where the line passing through the center of the pseudo-arc regarding as the anterior side line and the point most protruded in the direction perpendicular to the lateral direction on the anterior side line intersects the posterior side line. Thus it is easy to take the reference point in the lateral direction which is in the middle position between the center of figure of the epiphysis opening and the center of figure of the diaphysis opening, and from which the distance to the crotch side line is approximately equal to the distance to the counter-crotch side line and reference point in the direction perpendicular to the lateral direction which is in the middle position between the center of figure of the epiphysis opening and the center of figure of the diaphysis opening, and from which the distance to the anterior side line is approximately equal to the distance to the posterior side line.

The ratio of the distance from said straight segment to the alternative reference point in the lateral direction taken between said straight segment and said reference point in the lateral direction to the distance from the straight segment to said reference point in the lateral direction, is defined by bending ratio $\alpha$ on the plane along the lateral direction, and the ratio of the distance from the straight segment to the alternative reference point in the direction perpendicular to the lateral direction taken between said straight segment and said reference point in the direction perpendicular to the lateral direction to the distance from the straight segment to said reference point in the direction perpendicular to the lateral direction, is defined by bending ratio $\beta$ on the plane along the direction perpendicular to the lateral direction, so that any type of stems can be made whose curvature is from 0 to a maximum, as a reference stem and alternative stems, by selecting any value of $0 \leq \alpha \leq 1$ and any value of $0 \leq \beta \leq 1$. In each case of some typical curvatures of stem, giving examples of the shapes and the sizes of stems and deep hollows and the inserting position and posture of stem every step helps the surgeon to grasp the tendency of movement of the stem during inserting into the deep hollow so as to carry out his plan and to have the idea for some improved variations to meet his demand as well.

Confirming the tendency of movement of the stem in response to the bending ratio $\alpha$ on the plane along the lateral direction and the bending ratio $\beta$ on the plane along the direction perpendicular to the lateral direction in each case that the imaginary rasp is pushed into the imaginary three dimensional deep hollow, the surgeon changes somewhat the numerical value of $\alpha$ and $\beta$ of the stem so as to obtain the re-alternative stem which is his ideal or close to it by referring to his own ability and the current condition of the femur. Learning the transition of the positions and postures of the stem before the surgery enables him to operate with grasping the ideal course of the surgery.

In each case of the several reliable curvature of the stem, examples of the shape and the size of each stem and deep hollow and of the position and the posture of the stem implanted into the hollow of every step are shown to the surgeon so as to grasp the movement of the stem while pushing the stem into the hollow, making it easy for the surgeon to make clear his own demands for the stem and to have variations reflecting the demands.

After pushing the reference stem, the alternative stem and/or re-alternative stem into the imaginary three dimensional deep hollow, calculating the rates of Fit and Fill (the rate of contact the stem with the periphery of the deep hollow/the rate of area occupation of stem in the cross section of the deep hollow) of each section of the stem along the reference line enables the surgeon to know not only the positions and the postures of the stem of each case but the duration for fixing by Bone-Growth and the rates of Fit and Fill at the part for transmitting the load to the femur.

BRIEF DESCRIPTION OF SYMBOLS

1: femur, 2: epiphysis, 3: diaphysis, 4: deep hollow, 5: stem, 6: medullary cavity, 7: imaginary three dimensional deep hollow, 8: crotch side line, 9: counter-crotch side line, 10: anterior side line, 11: posterior side line, 13: epiphysis opening, 14: diaphysis opening, 15: provisional three dimensional reference deep hollow, 16: pattern of provisional deep hollow on the plane including the crotch and counter-crotch side lines, 17: pattern of provisional deep hollow on the plane including the anterior and posterior side lines, 18: provisional three dimensional reference stem, 19: reference arc on the plane including the crotch and counter-crotch side lines, 20: reference arc on the plane including the anterior and posterior side lines, 21: pseudo-arc regarding as the crotch side line, 22: pseudo-arc regarding as anterior side line, 25: small arc on the plane including the crotch and counter-crotch side lines, 26: large arc on the plane including the crotch and counter-crotch side lines, 27: small arc on the plane including the anterior and posterior side lines, 28: large arc on the plane including the anterior and posterior side lines, 29: body surrounded by four side planes, 30: quasi-circular cylinder, 31: imaginary three dimensional stem, 32: body, 33: nose, 34: portion of epiphysis, 35: residual portion of provisional three dimensional reference stem, 36: principal axis of inertia, 37: portion of diaphysis, 38: residual portion of provisional three dimensional reference deep hollow, 39: principal axis of inertia, 40: arrow, 41: transitional values, 42: greater trochanter, 43: non-overlapping part, 44: reference stem, 45: finished stem, 46: rasp, 46a: nose, 47: a series of pictures, 51: straight segment, 52: alternative reference arc on the plane including the crotch and counter-crotch side lines, 53: alternative small arc on the plane including the crotch and counter-crotch side lines, θm: angle of opening, θn: angle of opening, H: center of figure, J: center of figure, Ls: length of stem, F: reference point in the lateral direction, Fr: reference point in the direction perpendicular to the lateral direction, Gs: center of gravity, Gh: center of gravity, D: center, C: point most protruded in the lateral direction on the crotch side line, E: cross point, Dr: center, Cr: point most protruded in the direction perpendicular to the lateral direction on the anterior side line, Er: cross point, A: end point of epiphysis, B: end point of diaphysis (occupied position), Gr: end point of epiphysis, Err: cross point, L: terminal point of small arc, M: terminal point of large arc, B, Br, I, Ir: end point of diaphysis (occupied position), Fa, Fb: alternative reference point in the lateral direction.

BEST MODE FOR CARRYING OUT THE INVENTION

Figure 1:
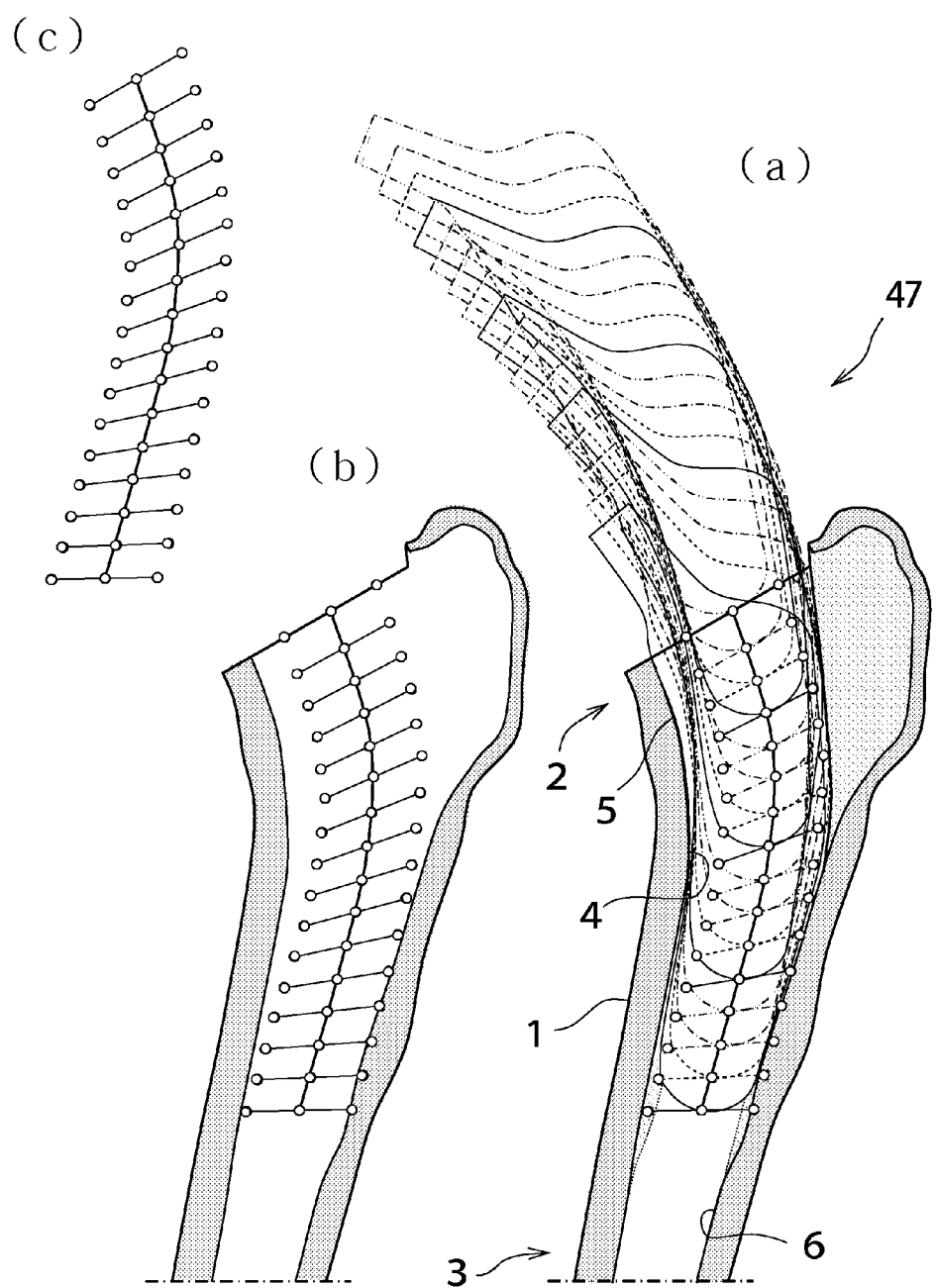
[FIG. 1]: a diagram of the configuration for implanting and/or pulling the stem into and/or out of the deep hollow and of positions and postures applied to the stem, which is obtained by the method of determining the shape of an artificial cement-less hip prosthesis stem according to the present invention.

The method of determining the shape of an artificial cement-less hip prosthesis stem according to the present invention is disclosed referring to the drawings, as follows: FIG. 1(a) is a successive illustration, wherein an artificial cement-less hip prosthesis stem 5 which is effectively to be united with a femur by Bone-Growth is implanted into a deep hollow 4 formed from the epiphysis 2 of a femur 1 toward the diaphysis 3 or the stem 5 is pulled out of the deep hollow 4.

Figure 2:
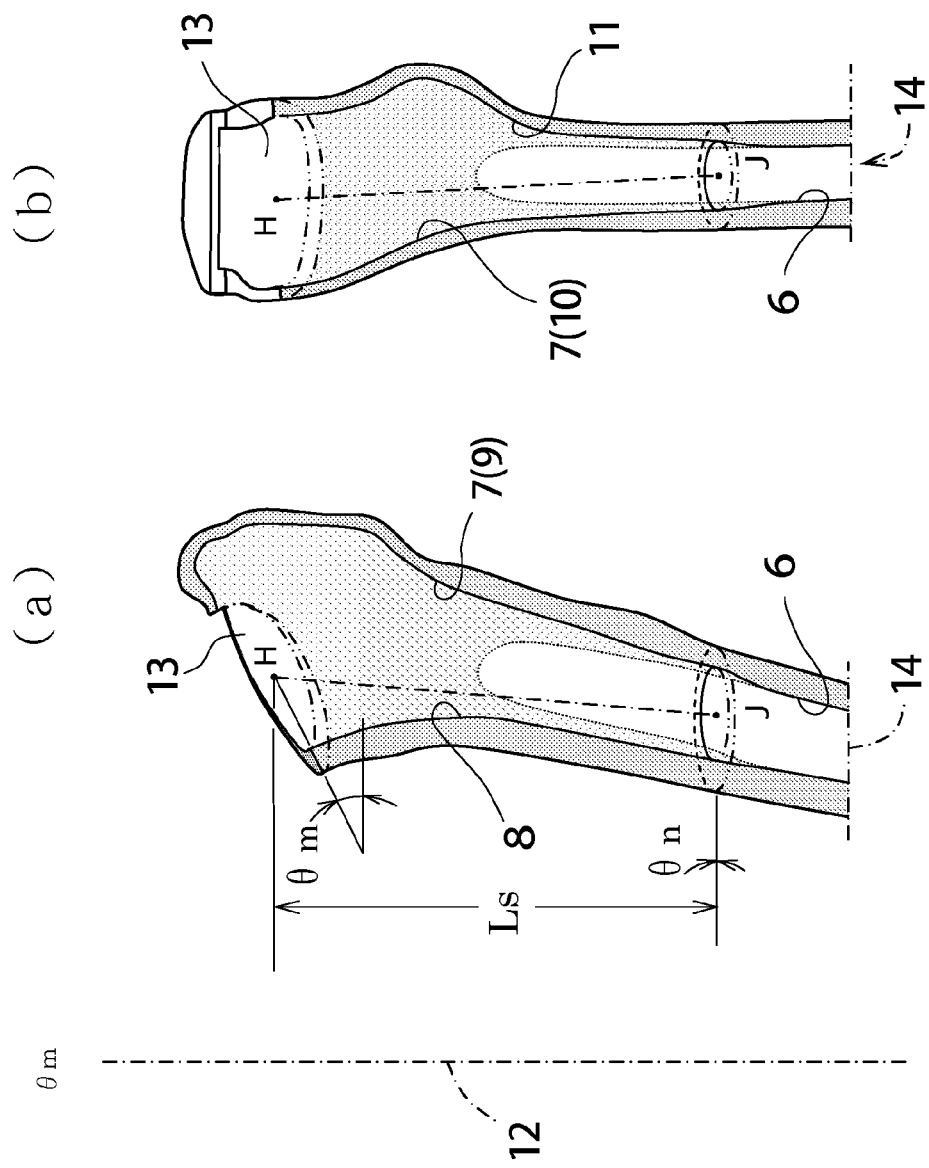
[FIG. 2]: an explanatory diagram to set the co-ordinates for forming a deep hollow in a femur.
Figure 28:
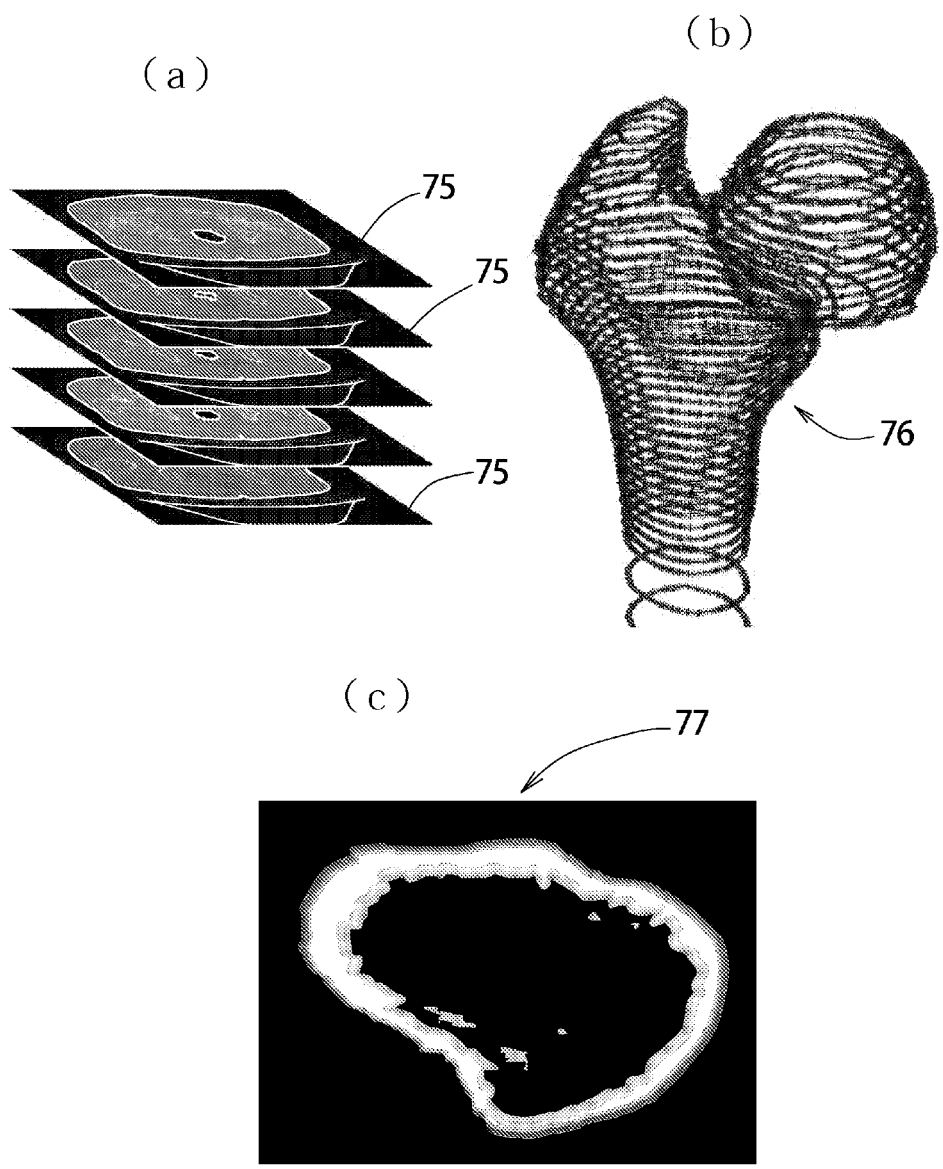
[FIG. 28]: explanatory diagrams of the way of processing the CT graphics of the femur.
Figure 29:
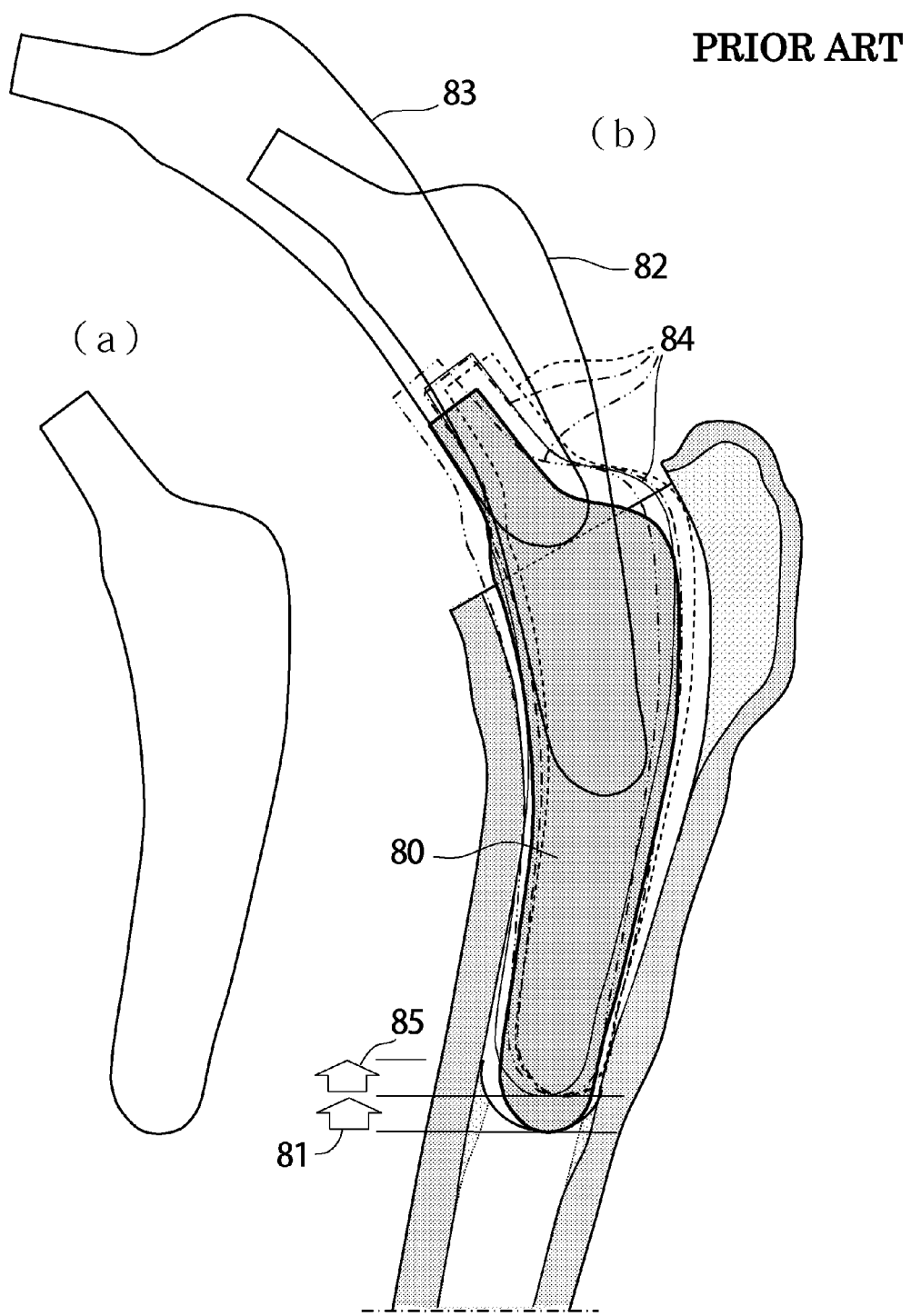
[FIG. 29]: an explanatory diagram to remove the stem from the femur.

Three dimensional graphics data are obtained from the femur 1 to have prosthesis by the method mentioned in FIG. 28. From these graphics data, a limitary thickness of the bony tissue is detected for forming the wall of the deep hollow in the femur. Referring to the limitary thickness, the shape of the imaginary three dimensional deep hollow 7 shown in FIG. 2 is calculated, which extends to the medullary cavity 6, and at the same time the coordinates of crotch side line 8 and of counter-crotch side line 9 which regulate the shape of lateral section of the imaginary deep hollow 7, which is shown in FIG. 2(a), and the coordinates of anterior side line 10 and of posterior side line 11 which regulate the shape of section perpendicular to the lateral section of the deep hollow 7, which is shown in FIG. 2(b), are introduced into the femur.

Figure 26:
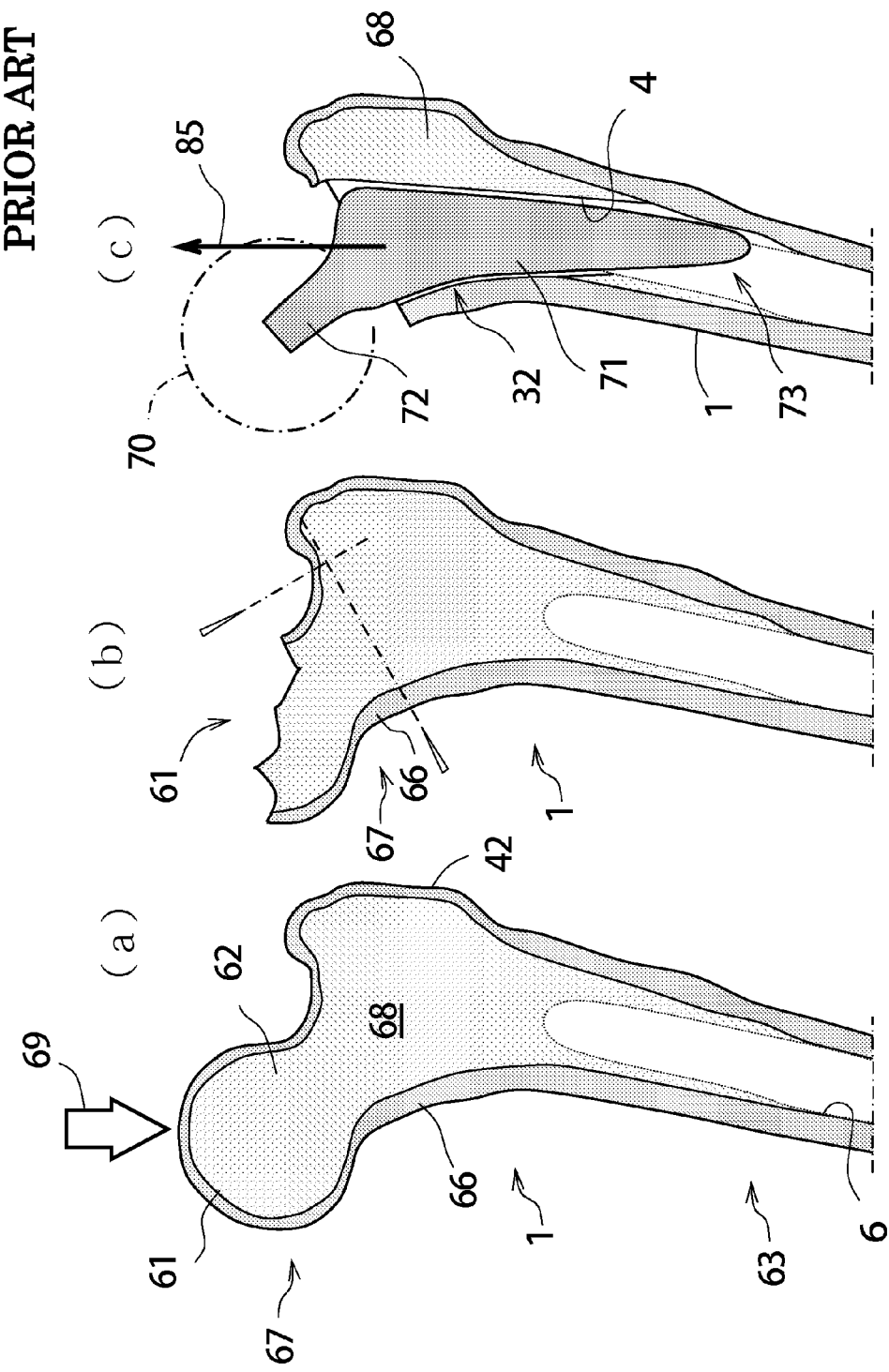
[FIG. 26]: a diagram of the way to move the stem.
Figure 27:
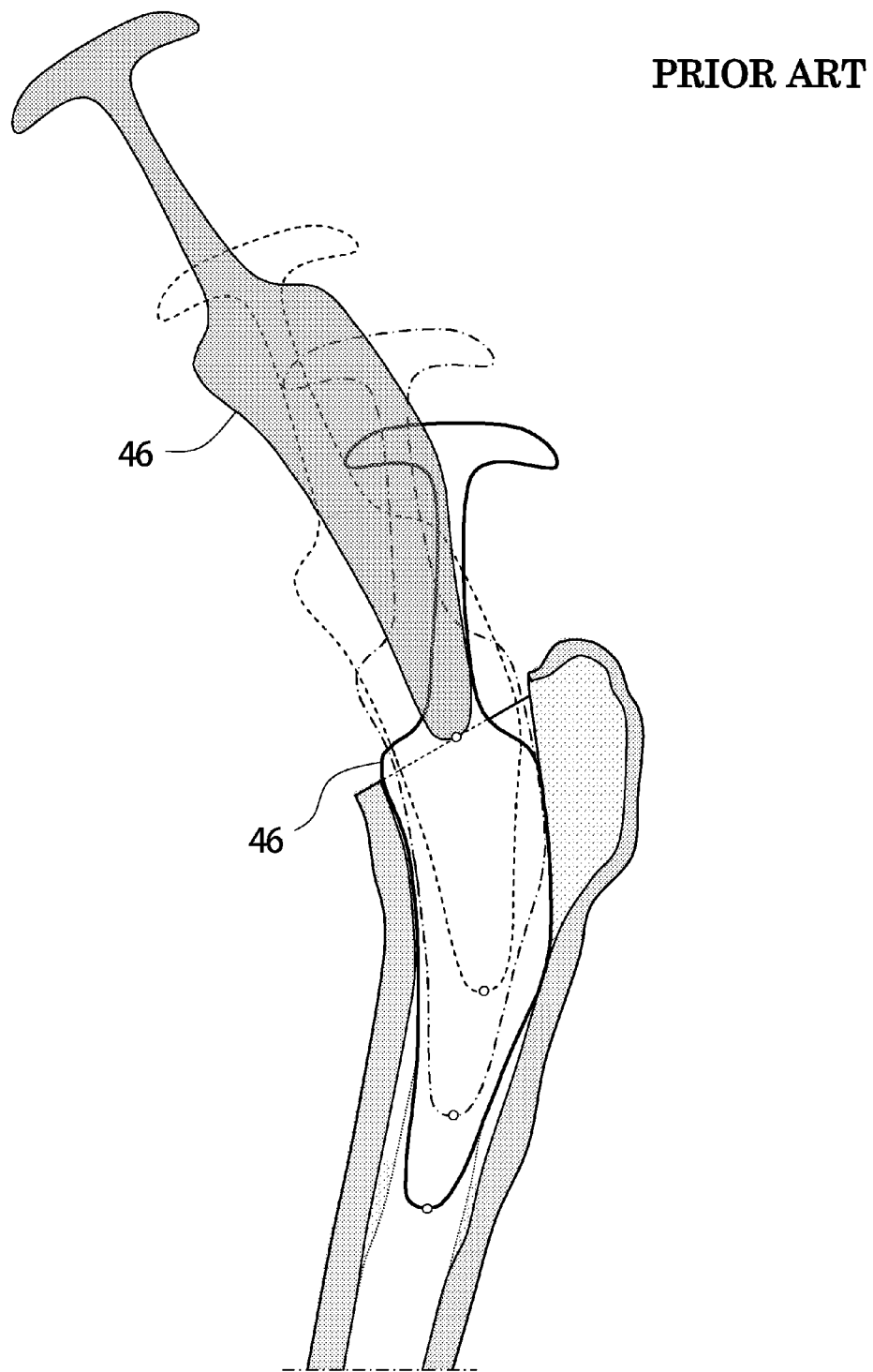
[FIG. 27]: a diagram of handling the rasp.

As explained in FIG. 26, the boundary line of the femur is decided for removing the damaged portion of the femur, where an opening is formed which enables a stem to be inserted. In order to form the opening, a reference line 12 is given so as to be parallel to the longitudinal direction of the femur 1, as shown in FIG. 2(a). From the position and the opening angle θm of the epiphysis opening 13 determined on the basis of the reference line, the shape and the center H of figure are calculated of the opening 13 of the imaginary three dimensional deep hollow 7. And, from the length of the stem Ls to be applied to the femur 1 and the opening angle θn of diaphysis, the shape and the center J of figure are calculated of the diaphysis opening 14 of the imaginary three dimensional deep hollow 7. The reference line 12 is chosen as the vertical line of the patient's body when standing up straight.

Figure 3:
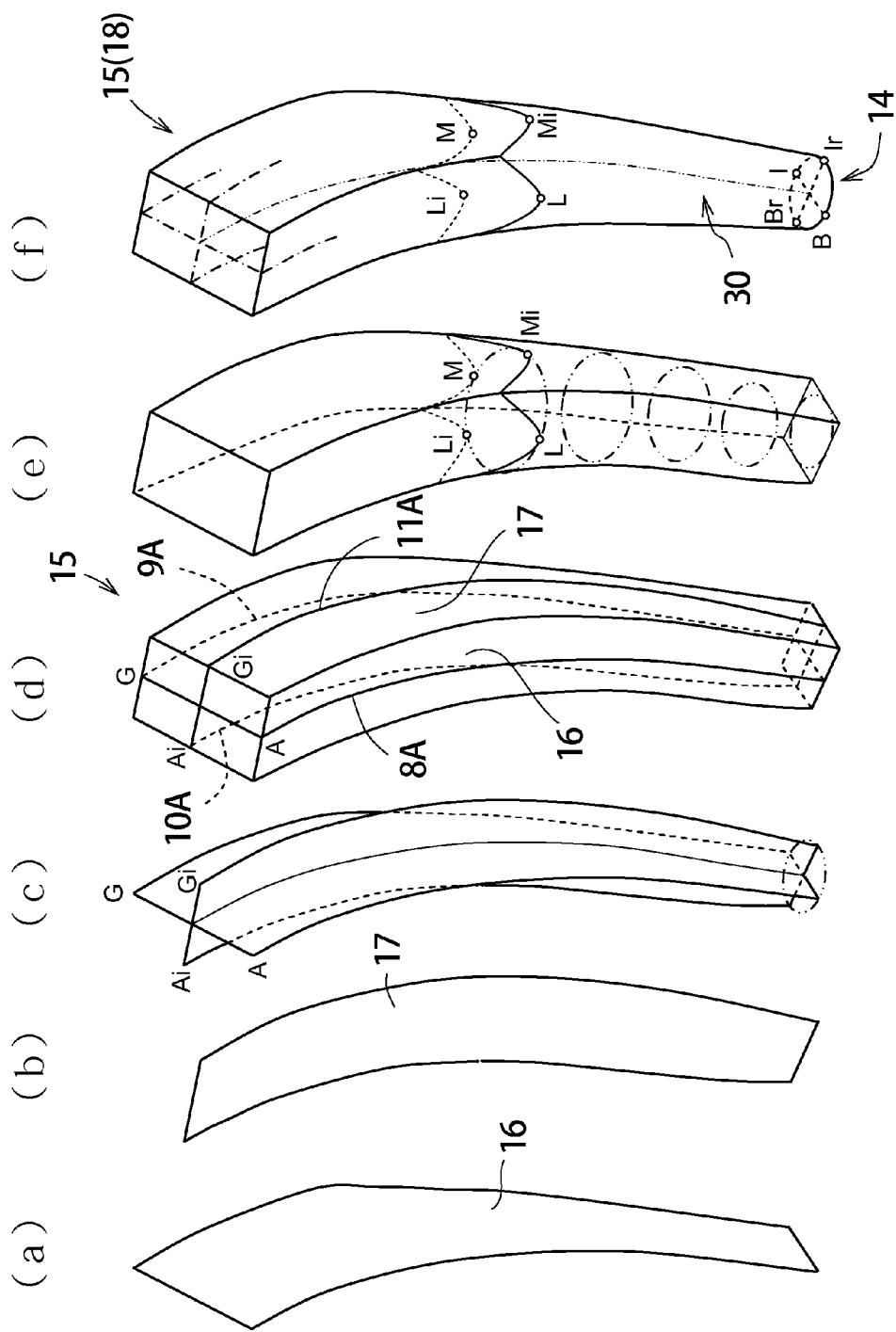
[FIG. 3]: models of the deep hollow and the stem for calculating.

In order to make a provisional three dimensional reference deep hollow 15 shown in FIG. 3(f), a pattern of provisional deep hollow 16 on the plane including the crotch and counter-crotch side lines, shown in FIG. 3(a), and a pattern of provisional deep hollow 17 on the plane including the anterior and posterior side lines, shown in FIG. 3(b), are obtained beforehand. The provisional three dimensional reference deep hollow 15 is a substitutive deep hollow on calculation of the imaginary three dimensional deep hollow 7, whose complicated shape is simplified by substituting a simple curvature for the various curvatures of all portions on the condition that the figure characteristic of the femur is kept, so that the positions and the postures of the stem can be determined every step of pulling the stem. FIG. 3 (f) represents not only the provisional three dimensional reference deep hollow 15 but the provisional three dimensional reference stem 18 having the same shape as the deep hollow.

As shown in FIG. 3 (d), the provisional deep hollow 16 mentioned above is a cross section of the provisional three dimensional reference deep hollow 15 cut by a plane including the crotch side line 8A and the counter-crotch side line 9A which are in the lateral direction of the deep hollow 15, and the provisional deep hollow 17 mentioned above is a cross section of the provisional three dimensional reference deep hollow cut by a plane including the anterior side line 10A and the posterior side line 11A which are in the direction perpendicular to the lateral direction of the deep hollow. By arranging these two deep hollows 16 and 17 as described later, the provisional three dimensional reference deep hollow 15 is formed. Substituting this provisional three dimensional deep hollow for the imaginary three dimensional deep hollow makes possible calculating itself, moreover possible it in several hours even by a personal computer.

Figure 5:
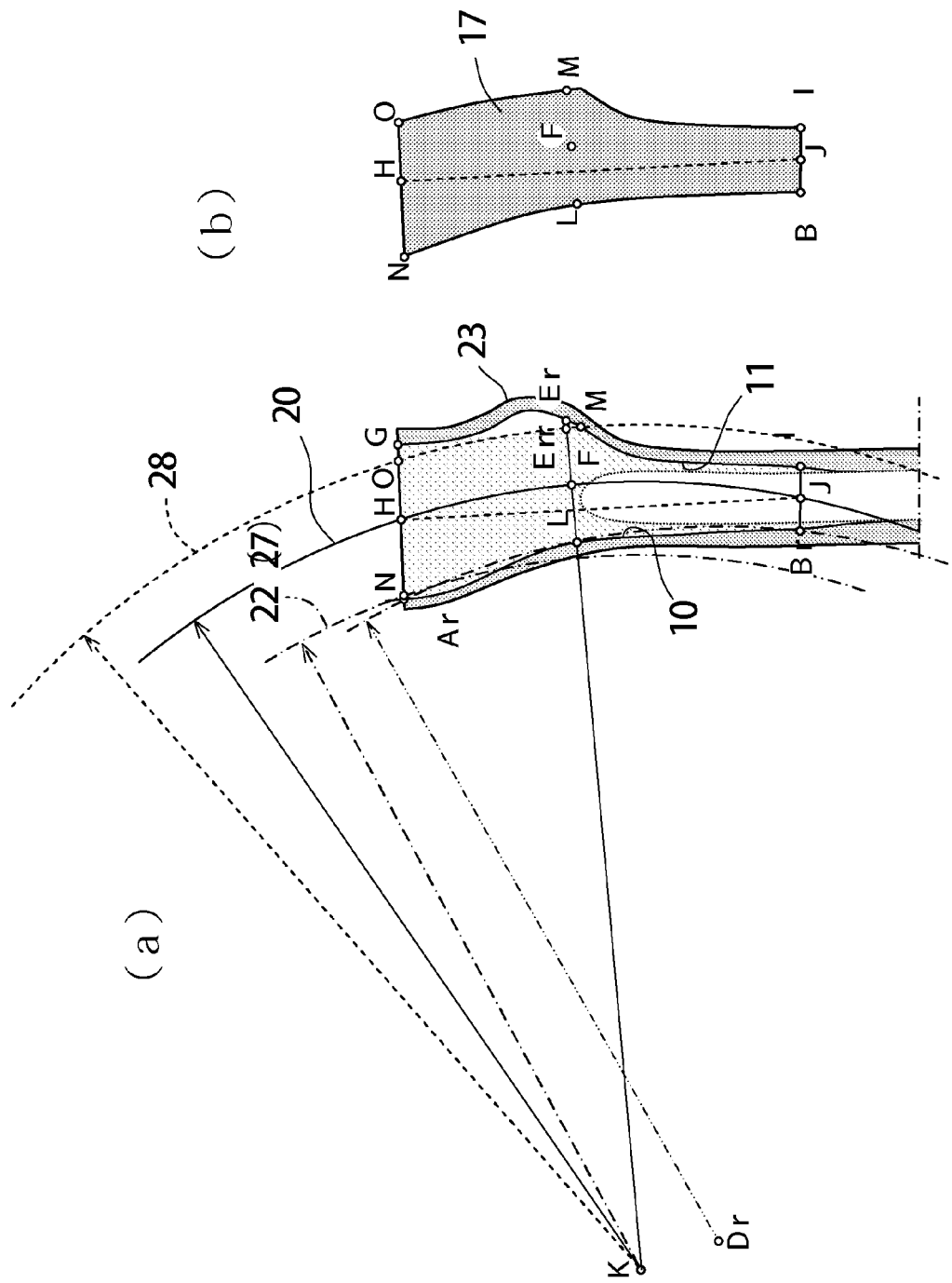
[FIG. 5]: an explanatory diagram to set the co-ordinates for forming a deep hollow in a femur.
Figure 6:
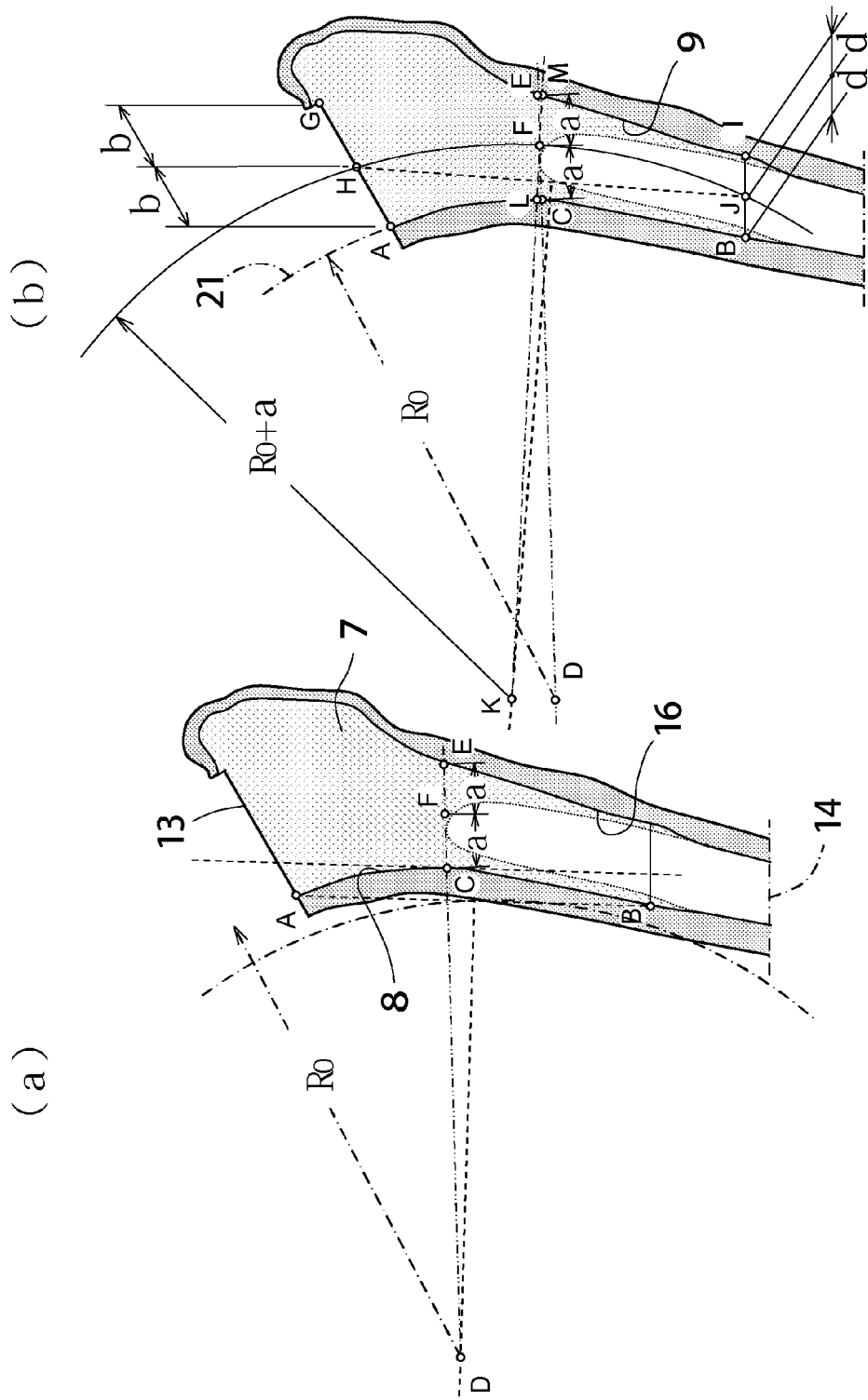
[FIG. 6]: an explanatory diagram to set the co-ordinates for forming a deep hollow in a femur.
Figure 7:
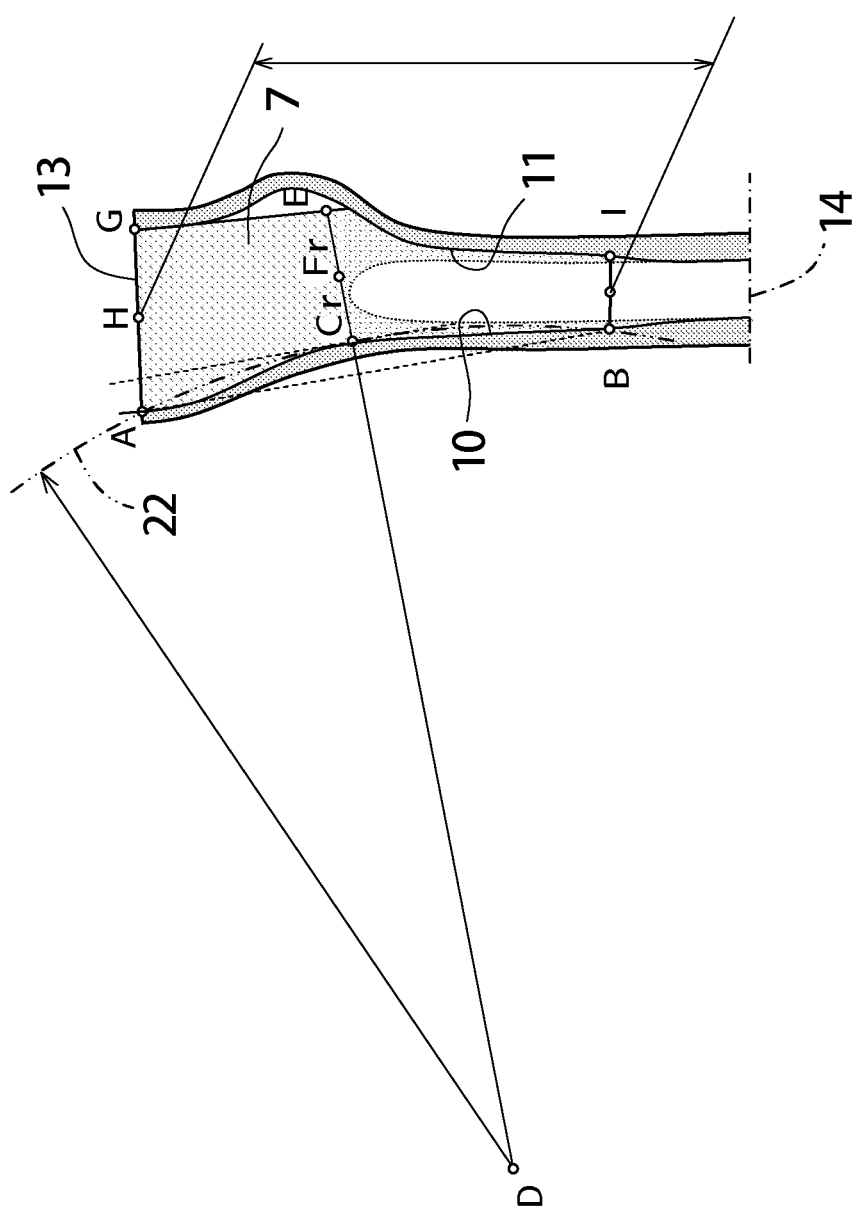
[FIG. 7]: an explanatory diagram to set the co-ordinates for forming a deep hollow in a femur.

In order to obtain the provisional deep hollow 16 on the plane including the crotch and counter-crotch side lines and the provisional deep hollow 17 on the plane including the anterior and posterior side lines, a reference arc 19 on the plane including the crotch and counter-crotch side lines shown in FIG. 4(a) which passes through a reference point F in the lateral direction, and a reference arc 20 on the plane including the anterior and posterior side lines shown in FIG. 5(a) which passes through a reference point Fr in the direction perpendicular to the lateral direction are calculated. The reference point F in the lateral direction, as shown in FIG. 6(a), lies halfway in the vertical direction between the epiphysis opening 13 and the diaphysis opening 14 and at the point where the distance 'a' from the point to the crotch side line 8 is approximately equal to the distance 'a' from the point to the counter-crotch side line 9. The reference point Fr, as shown in FIG. 7, lies halfway in the vertical direction between the epiphysis opening 13 and the diaphysis opening 14 and at the point where the distance to the anterior side line 10 is approximately equal to the distance to the posterior side line 11.

In the present case, in order to realize the bend of the deep hollow, the reference point F in the lateral direction, as shown in FIG. 6(b), is the midpoint of the line from the point C most protruded in the lateral direction on the crotch side line to the cross point E where the line passing through the center point D of the pseudo-arc 21 regarding as the crotch side line and the point C most protruded in the lateral direction on the crotch side line intersects the counter-crotch side line 9. The reference point Fr in the direction perpendicular to the lateral direction, as shown in FIG. 5(a), is the midpoint of the line from the point Cr most protruded in the direction perpendicular to the lateral direction on the anterior side line to the cross point Er where the line passing through the center point Dr of the pseudo-arc 22 regarding as the anterior side line and the point Cr most protruded in the direction perpendicular to the lateral direction on the anterior side line intersects the posterior side line 11. But in the case that the point Er is in the lesser trochanter 23, the reference point Fr in the direction perpendicular to the lateral direction is close to the posterior too much, so that Err may be preferably substituted for the point Er, where the posterior side line 11 intersects the line parallel to the line linking the end point A of epiphysis A and the end point B of diaphysis on the anterior side line 10 and passing through the end point Gr of epiphysis on the posterior side line 11, as shown in FIG. 7. This is unavoidable in order to take no account of the existence of the lesser trochanter 23, but on the contrary, preferable in order to keep the bending characteristic of the provisional deep hollow 17 on the plane including the anterior and the posterior side lines.

As shown in FIG. 6(a), the pseudo-arc 21 regarding as the crotch side line mentioned above passes three points; an end point A of epiphysis and an end point B of diaphysis lying on the crotch side line 8 of the imaginary three dimensional deep hollow 7, and the point C most protruded in the lateral direction on the crotch side line, where the line parallel to the straight line passing through these two points A and B contacts the crotch side line 8. The pseudo-arc 22 regarding as anterior side line, as shown in FIG. 7, passes three points; an end point A of epiphysis and an end point B diaphysis on the anterior side line 10 of the imaginary three dimensional imaginary deep hollow 7, and the point Cr most protruded in the direction perpendicular to lateral direction on the anterior side line where the line parallel to the straight line passing through these two points A and B contacts the anterior side line 10. These pseudo-arcs are in the part of the femur where its curvature is the maximum, which means that there is no curvature exceeding this maximum curvature neither on the plane including the crotch and counter-crotch side lines nor on the plane including the anterior and posterior side lines. Even if a large curvature is given to the deep hollow, the calculation may be limited only up to the provisional three dimensional reference deep hollow 15 (see FIG. 3(f)) including the pseudo-arc 21 regarding as the crotch side line and the pseudo-arc 22 regarding as anterior side line.

The pattern 16 of provisional deep hollow on the plane including the crotch and counter-crotch side lines mentioned above, which is shown in FIG. 4(b), is formed inside the imaginary three dimensional deep hollow 7, as illustrated in FIG. 4(a), which is surrounded by a small arc 25 on the plane including the crotch and counter-crotch side lines which is concentric with the reference arc 19 on the plane including the crotch and counter-crotch side lines and has a radius Ro which is shorter than the radius of the reference arc 19 and longer than the distance to the end point A of epiphysis on the crotch side line, a large arc 26 on the plane including the crotch and counter-crotch side lines which is concentric with the reference arc 19 and has a radius Ro+2b which is longer than the radius of the reference arc 19 and shorter than the distance to the end point G of epiphysis on the counter-crotch side line, the crotch side line 8 which is from the terminal point L of the small arc where the small arc 25 intersects the crotch side line 8 to the end point B of diaphysis on the crotch side line 8, and the counter-crotch side line 9 which is from the terminal point M of the large arc where the large arc 26 intersects the counter-crotch side line 9 to the end point I of diaphysis lying on the counter-crotch side line 9.

The pattern 17 of provisional deep hollow on the plane including the anterior and posterior side lines mentioned above, which is shown in FIG. 5(*b*), is formed inside the imaginary three dimensional deep hollow 7, as illustrated in FIG. 5(*a*), which is surrounded by a small arc 27 on the plane including the anterior and posterior side lines which is concentric with the reference arc 20 on the plane including the anterior and posterior side lines and has a radius which is shorter than the radius of the reference arc and longer than the distance to the end point Ar of epiphysis on the anterior side line 10, a large arc 28 on the plane including the anterior and posterior side lines which is concentric with the reference arc 20 and has a radius which is longer than the radius of the reference arc 20 and shorter than the distance to the end point Gr of epiphysis on the posterior side line 11, the anterior side line 10 which is from the terminal point Lr of small arc where the small arc 27 intersects the anterior side line 10 to the end point Br of diaphysis on the anterior side line 10, and the posterior side line 11 which is from the terminal point M of large arc end point where the large arc 28 intersects the posterior side line 11 to the end point Ir of diaphysis on the posterior side line 11.

Figure 4:
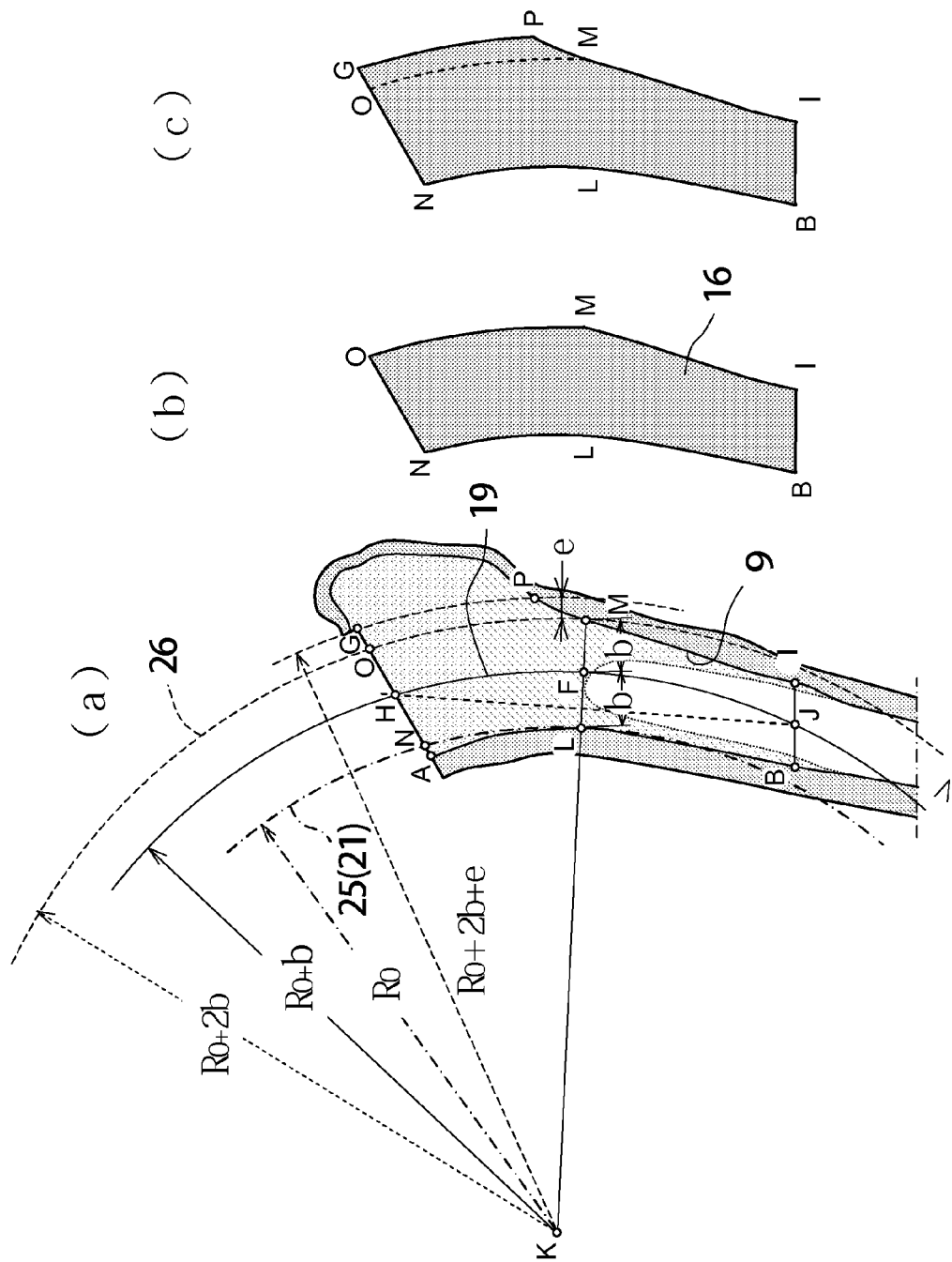
[FIG. 4]: an explanatory diagram to set the co-ordinates for forming a deep hollow in a femur.

In FIG. 4(*a*), the radius of the small arc 25 on the plane including the crotch and counter-crotch side lines is equal to the radius of the pseudo-arc 21 regarding as the crotch side line. In FIG. 5(*a*), the radius of the small arc 27 on the plane including the anterior and posterior side lines is equal to the radius of the pseudo-arc 22 regarding as anterior side line. The radius of the small arc 25 on the plane including the crotch and counter-crotch side lines (see FIG. 4 (*a*)) is defined by Ro, consequently the radius of the reference arc 19 on the plane including the crotch and counter-crotch side lines is defined by Ro+b, and the radius of the large arc 26 on the plane including the crotch and counter-crotch side lines is defined by Ro+2*b*, so that the point F is still the reference point in the lateral direction.

As shown in FIG. 4, the radius of the large arc 26 on the plane including the crotch and counter-crotch side lines is designed to have the length equal to the addition of the difference between the radius of the reference arc 19 on the plane including the crotch and counter-crotch side lines passing through the reference point F in the lateral direction and the radius of the small arc 25 on the plane including the crotch and counter-crotch side lines to the radius of the reference arc 19 on the plane including the crotch and counter-crotch side lines. As shown in FIG. 5, the radius of the large arc 28 on the plane including the anterior and posterior side lines is designed to have the length equal to the addition of the difference between the radius of the reference arc 20 on the plane including the anterior and posterior side line passing through the reference point Fr in the direction perpendicular to the lateral direction and the radius of the small arc 27 on the plane including the anterior and posterior side line to the radius of the reference arc 20 on the plane including the anterior and posterior side lines. Thereby, the calculation which is for the space in the greater trochanter 42 and the lesser trochanter 23 where the stem does not occupy can be eliminated beforehand from calculating the transitional values of the positions and postures of the provisional three dimensional reference stem 18.

The circular arc 26 on the plane including the crotch and counter-crotch side lines of FIG. 4 (*a*) has a radius which is shorter than the distance to the end point G of epiphysis on the counter-crotch side line 9, but may have a longer radius that passes through the end point G of epiphysis on the counter-crotch side line 9. In this case, the pattern 16 of provisional deep hollow on the plane including the crotch and counter-crotch side lines is illustrated as shown in FIG. 4(*c*), where the part surrounded by points O, M, P and G in the figure is added to the original pattern. In order not to take much time for calculating every step mentioned after, the pattern 16 of provisional deep hollow on the plane including the crotch and counter-crotch side lines can be used which is shown in FIG. 4(*b*), for the calculation is scarcely influenced by adding the part surrounded by the points O, M, P and G, as far as the curvature is fixed on calculating.

The provisional three dimensional reference stem 18, shown in FIG. 3(*f*) is made. This is formed so as to be the body 29 surrounded by four side planes, by arranging the patterns 16 of the provisional deep hollow on the plane including the crotch and counter-crotch side lines of FIG. 3(*a*) on the anterior side line 10A and the posterior side line 11A of FIG. 3(*d*), respectively, so as to face each other, and the patterns 17 of the provisional deep hollow on the plane including the anterior and posterior side lines of FIG. 3(*b*) on the crotch side line 8A and the counter-crotch side line 9A, respectively, so as to face each other. But as shown in FIG. 3(*e*), the quasi-circular cylinder 30 is given to the body, which has the same shape as the imaginary three dimensional deep hollow 7 corresponding to the region from the terminal points L and Li of the small arc and the terminal points M and Mi of the large arc to the diaphysis opening 14, thus the reference stem 18 has the shape of FIG. 3(*f*).

Since the provisional three dimensional reference stem 18 contains the reference arc 19 on the plane including the crotch and counter-crotch side lines (see FIG. 4) and the reference arc 20 on the plane including the anterior and posterior side lines (see FIG. 5), it has the bend characteristic both in the lateral direction and in the direction perpendicular to the lateral direction of the stem. When the provisional three dimensional reference stem 18 is substituted for the imaginary three dimensional deep hollow 7 or the imaginary three dimensional stem 31 (not shown), the transitional values of the position and posture of the stem 18 while pulling the provisional three dimensional reference stem 18 out of the provisional three dimensional reference deep hollow 15 are almost the same as those of the imaginary three dimensional deep hollow 7 or the imaginary three dimensional stem 31. As shown in FIG. 3 (*f*), the provisional three dimensional reference stem 18 has the body surrounded by four side planes as a body 32 and the quasi-circular cylinder corresponding to the deep hollow as a nose 33, therefore a high rate of Fill can be given to the body of the reference stem mentioned after, and a high rate of Fit can be given to the nose of the stem.

Figure 8:
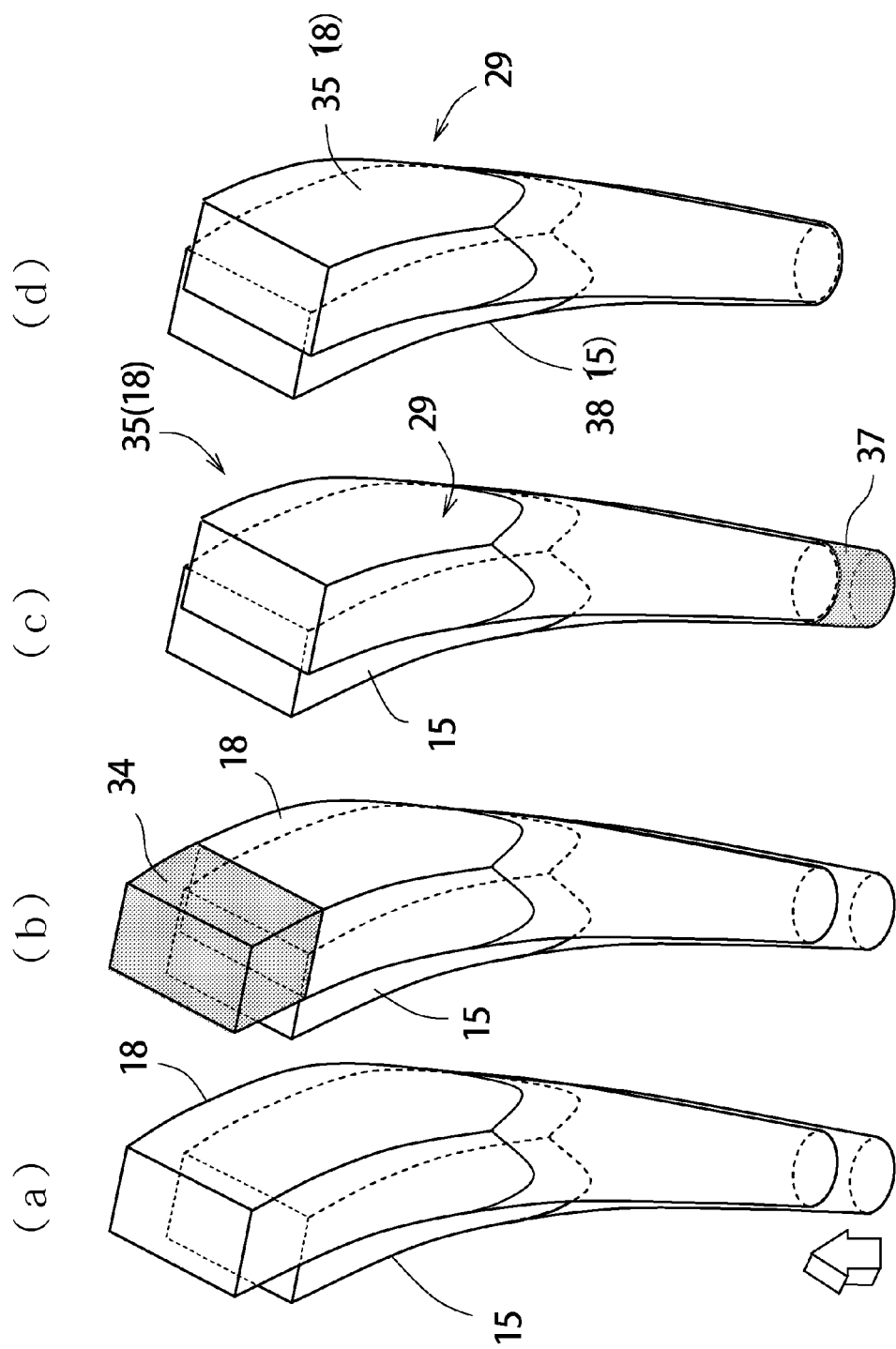
[FIG. 8]: a series of calculation models of the deep hollow and the stem.
Figure 9:
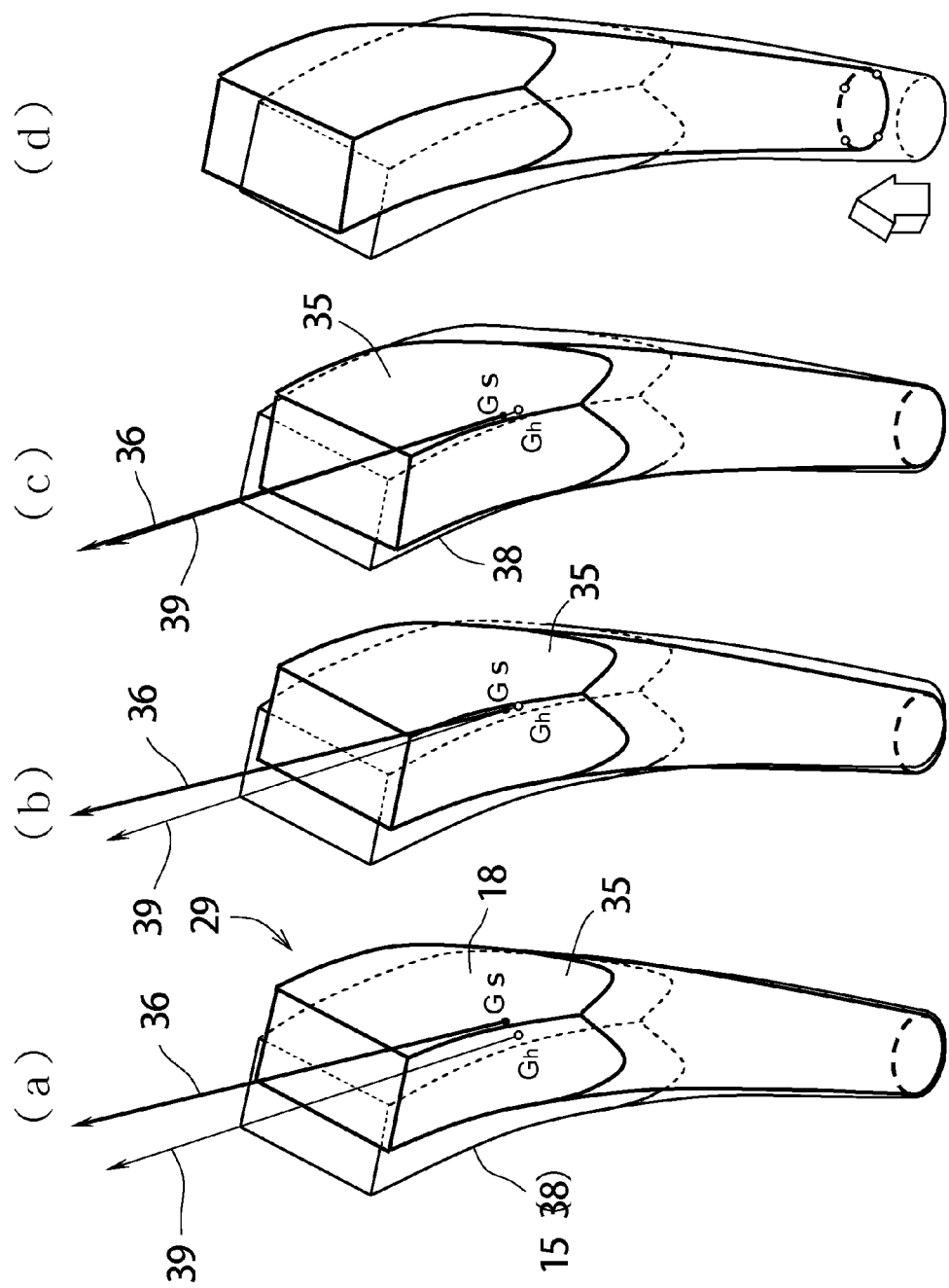
[FIG. 9]: a series of calculation models of the deep hollow and the stem.

The provisional three dimensional reference deep hollow 15 is made whose shape is the same as that of the provisional three dimensional reference stem 18. The position and posture of the provisional three dimensional reference deep hollow 15 is calculated every step that the stem 18 is gradually pulled out of the deep hollow 15 in the direction of the arrow shown in FIG. 8(*a*) and FIG. 9(*d*), at the constant rate of Ls/40 mentioned below. More particularly referring to FIG. 8, the stem 18 is pulled out of the deep hollow 15 to go through the process as follows; in the case that the number of the steps for pulling the stem is 40, for instance, the provisional three dimensional reference stem 18 is raised by Ls/40 in the provisional three dimensional reference deep hollow 15. When the length of the stem Ls is 100 mm, the stem is raised by 2.5 mm every step. The course of raising stem 18 every step will be mentioned later.

Raising the stem starts with the state of FIG. 3(*f*) that the provisional three dimensional reference stem 18 is settled in the provisional three dimensional reference deep hollow 15. The four occupied positions; B and Br, the end points of diaphysis on the crotch side line 8A and the anterior side line 10A, and I and Ir, the end points of diaphysis on the counter-crotch side line 9A and the posterior side line 11A of the provisional three dimensional reference stem 18, agrees with the provisional three dimensional reference deep hollow 15. In FIG. 8(a), the provisional three dimensional reference stem 18 is raised so as to be pulled by Ls/40. By removing the portion 34 of the epiphysis, the shadowed portion of the provisional three dimensional reference stem 18, which does not overlap the provisional three dimensional reference deep hollow 15, as shown in FIG. 8(b), the residual portion 35 of the provisional three dimensional reference stem is made as shown in FIG. 8(c). And the center Gs of gravity and the principal axes 36 of inertia of the residual portion 35 of the provisional three dimensional reference stem are calculated as illustrated in FIG. 9(a). The residual portion 38 of the provisional three dimensional reference deep hollow is made as illustrated in FIG. 8(d) by removing the shadowed the portion 37 of the diaphysis shown in FIG. 8(c), where the provisional three dimensional reference stem 18 does not overlap the provisional three dimensional reference deep hollow 15. As it stands, the center Gh of gravity and the principal axes 39 of inertia of the residual portion 38 of the provisional three dimensional reference deep hollow shown in FIG. 9(a) are calculated. The principal axes of inertia is illustrated only in the direction of pulling the stem but omitted in other directions.

As shown in FIG. 9(b), the residual portion 35 of the provisional three dimensional reference stem is moved to the residual portion 38 of the provisional three dimensional reference deep hollow so as to shift the center Gs of gravity of the residual portion 35 of the provisional three dimensional reference stem to the principal axes 39 of inertia of the residual portion 38 of the provisional three dimensional reference deep hollow on the condition that the posture of the stem is kept in the step. The residual portion 35 of the provisional three dimensional reference stem is rotated around the shifted center Gs of gravity in the direction of arrow 40, so that the principal axes 36 of inertia in the direction of pulling the residual portion 35 of the provisional three dimensional reference stem may coincide the principal axes 39 of inertia of the residual portion 38 of the provisional three dimensional reference deep hollow, as shown in FIG. 9(c), thereby the residual portion 35 of the provisional three dimensional reference stem and the residual portion 39 of the provisional three dimensional reference deep hollow will be maximally overlapped.

Figure 23:
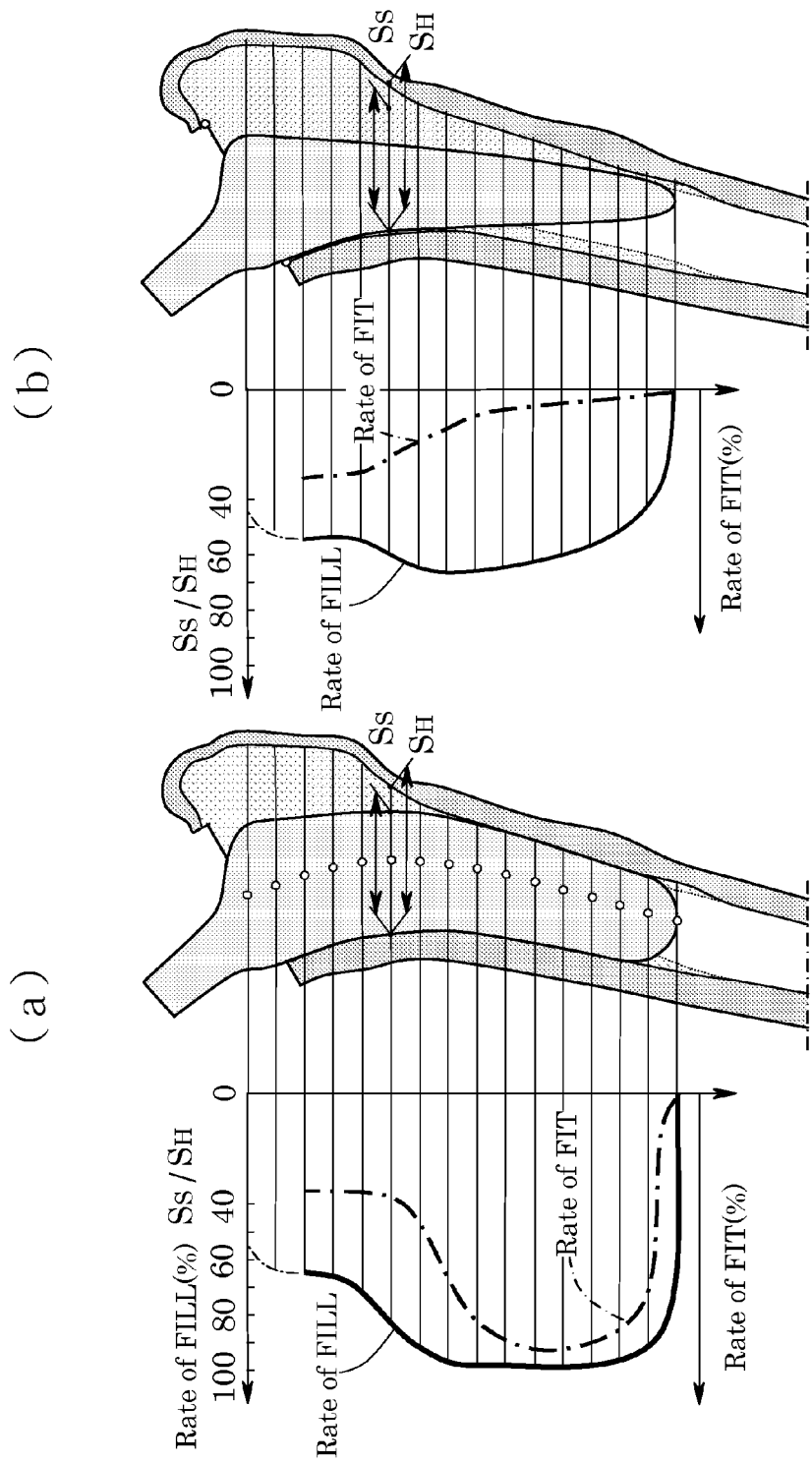
[FIG. 23]: an explanatory diagram of the rates of Fit and Fill.

Pulling the residual portion 35 of the provisional three dimensional reference stem out of the residual portion 38 of the provisional three dimensional reference deep hollow in a posture of the stem so as to be off as little as possible, makes the interference between them minimum, resulting in high rate of Fill displayed on the stem, in particular on the body 32 forming a body surrounded by four side planes. But the high rate of Fill is not effective on the portion from the body to the diaphysis, which corresponds to the portion of the provisional three dimensional reference deep hollow 15 as mentioned before, for the portion does not transmit the load in spite of the fact that the rate of Fill is higher than that of the body 32. What is noteworthy on the portion is that the capability for keeping the posture of the stem is considerably improved by increasing the rate of Fit. FIG. 23 is a two-dimensional illustration showing the characteristics mentioned above. Incidentally, the occupied positions of the four points, the end points B and Br of diaphysis and the end points I and Ir of diaphysis, of the lower end of the residual portion of the provisional three dimensional reference stem 35 are obtained.

Figure 11:
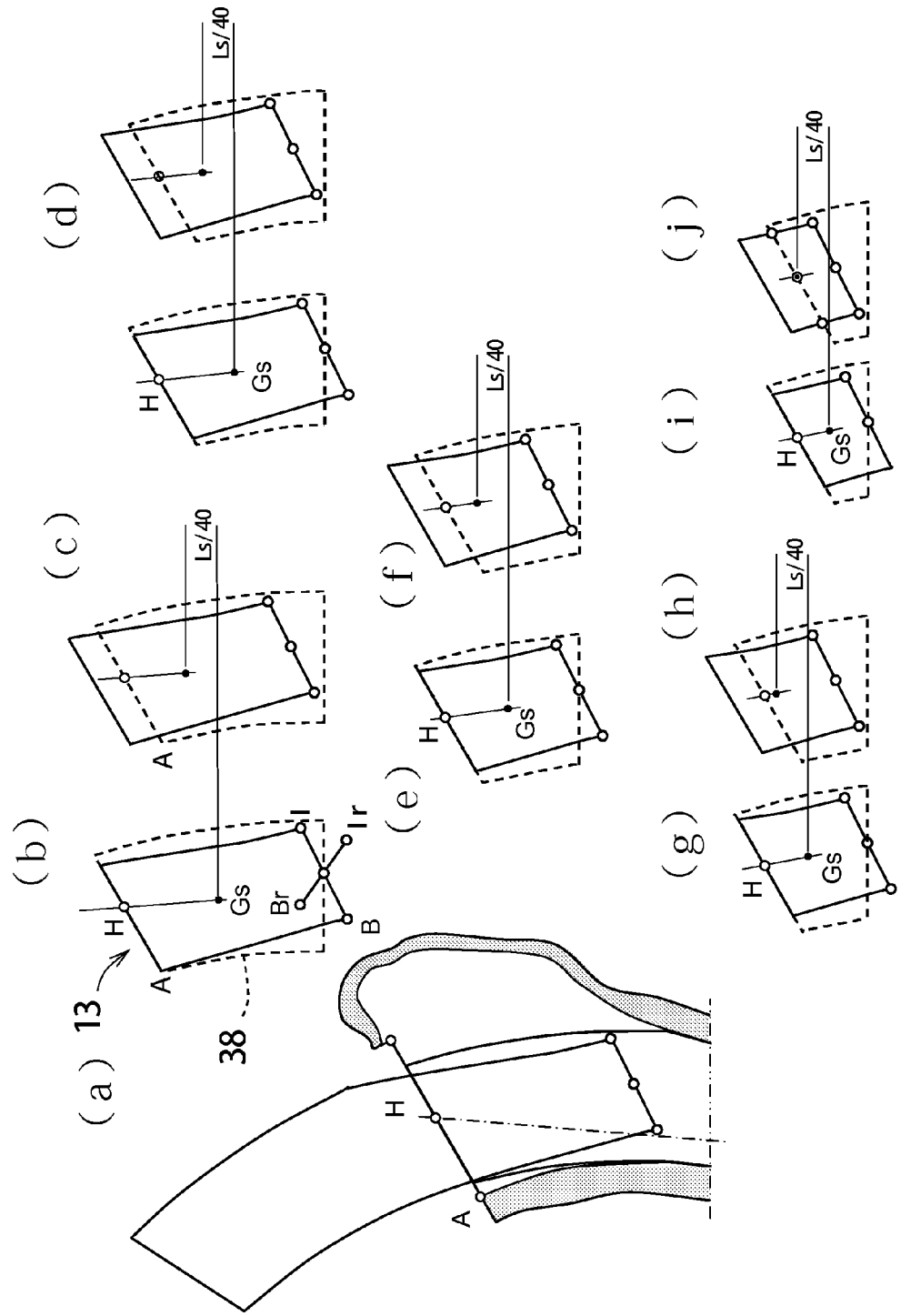
[FIG. 11]: a series of calculation models of the deep hollow and the stem.

In the latter half of the steps, both the residual portion 35 of the provisional three dimensional reference stem and the residual portion 38 of the provisional three dimensional reference deep hollow become short as shown in FIG. 11. Calculating to decide the direction of pulling the stem by detecting the principal axes of inertia can be done as far as the residual portion 35 of the provisional three dimensional reference stem and the residual portion 38 of the provisional three dimensional reference deep hollow are recognized as to be long objects in the direction of pulling the stem, therefore in the latter half of the steps, it is impossible to mathematically coincide the principal axes of inertia by rotating the stem. But at that point, the residual portion 35 of the provisional three dimensional reference stem moves in the space widening toward the epiphysis opening 13 of the residual portion 38 of the provisional three dimensional reference deep hollow. When the aspect ratio of the residual portions decreases to about 2, the calculation is switched as follows.

Referring to FIG. 11(b), the center Gs of gravity of the residual portion 35 of the provisional three dimensional reference stem is gradually moved to the epiphysis opening 13 along the line from the center Gs of gravity of the residual portion 35 of the provisional three dimensional reference stem to the center H of the figure of the epiphysis opening 13 of the imaginary three dimensional deep hollow 7, on the condition that the posture of the stem of every step is kept. The four points B, Br, I and Ir at the diaphysis are obtained every step, as the occupied position of the residual portion 35 of the stem. The occupied positions in the last step are lying around the center H of figure of the epiphysis opening 13. This means that the surgeon can confidently begin with placing a rasp at the center of the epiphysis opening to make a deep hollow. The rasp is pushed into the deep hollow on the condition that the posture thereof is kept for a while, therefore handling of the rasp is simple until the latter half of the steps for pushing the rasp into the hollow, that is, until the first half of the steps for pulling the stem out of the deep hollow. When the handling the rasp is complicated to excise spongiosa with the change of its posture, the rasp has already advanced deeply into the deep hollow, so that the rasp does not deviate from the course of pushing the stem into the hollow even if the rasp receives unnecessary force.

Figure 10:
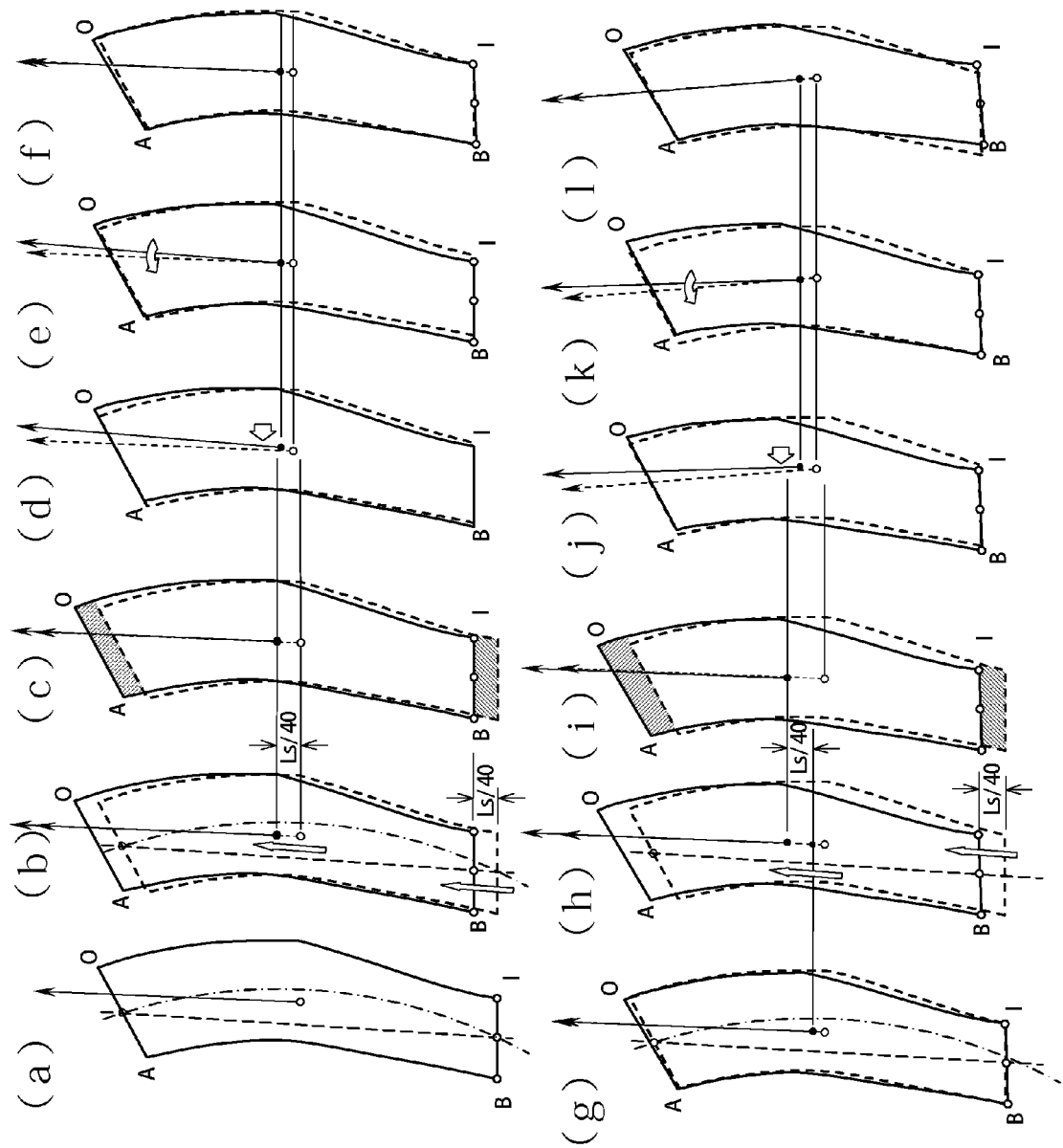
[FIG. 10]: a series of calculation models of the deep hollow and the stem.

The four points B, Br, I and Ir showing the occupied positions of the residual portion 35 of the provisional three dimensional reference stem rising in the provisional three dimensional reference deep hollow 15, show the movement of the four points of the three dimensional reference provisional stem 18. The data are put in storage from the steps of FIG. 8(d), FIG. 9(d), and all of FIG. 10 and FIG. 11. It is obvious that the transitional values of occupied positions of the four points specifies the change in the position and posture of the provisional three dimensional reference stem 18. By accumulating the data in order of the steps of the rise by Ls/40, a series of the data is obtained as shown in FIG. 1(a). The two-dimensional figures are shown by using only two points B and I, but actually more than three points are obtained as the occupied data every step, enabling the stem to move three dimensionally based on these data. For reference, the upper section of FIG. 10 shows the first step, the lower section shows the second step, (g) of the lower section is the same as (f) of the upper section for understanding the change from the upper section to the lower section. The provisional three dimensional reference deep hollow 15 is described by using the pattern of provisional deep hollow 16 on the plane including the crotch and counter-crotch side lines, and the provisional three dimensional reference stem 18 is described by using the pattern of provisional deep hollow 16 on the plane including the crotch and counter-crotch side lines.

Figure 12:
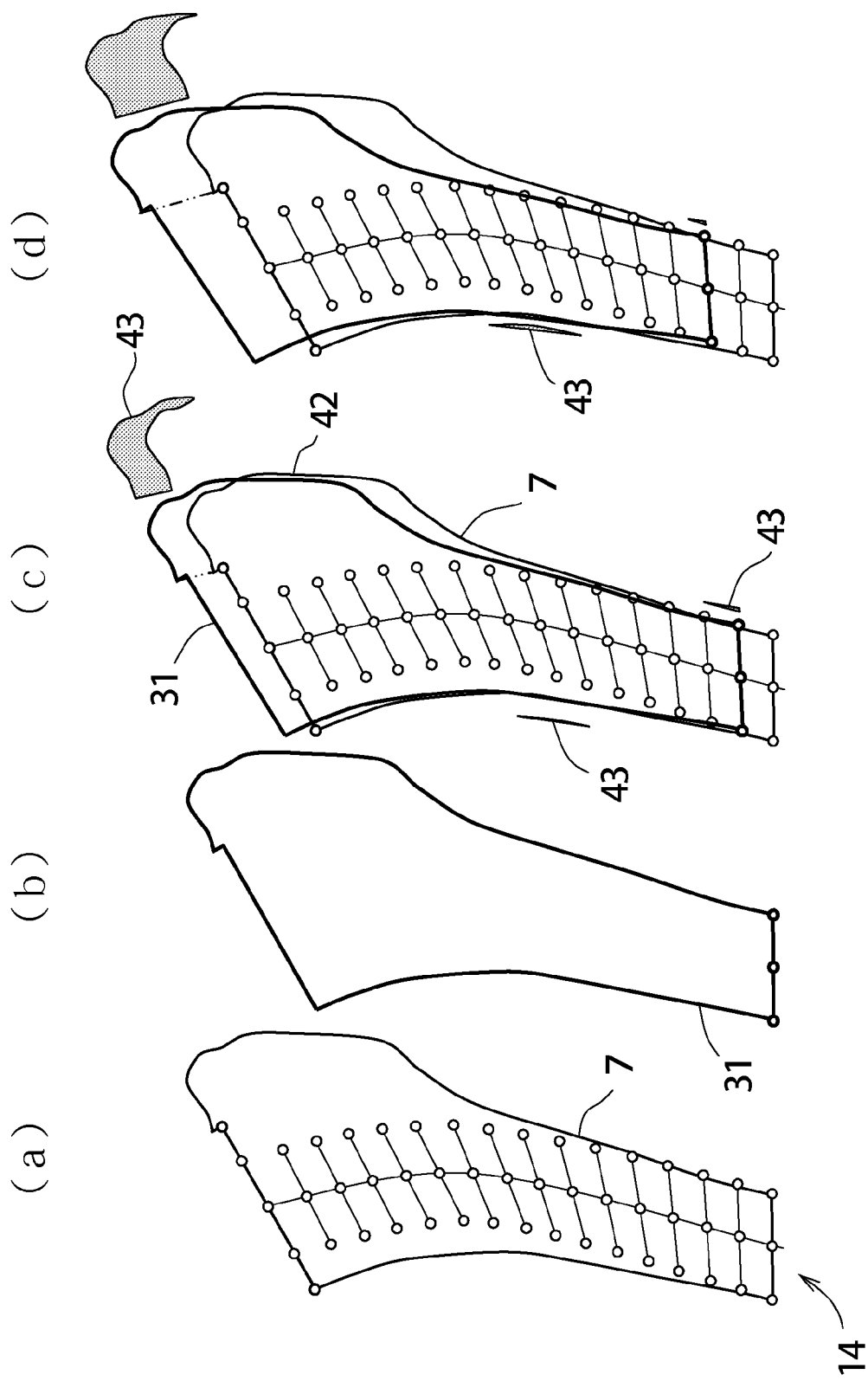
[FIG. 12]: a series of figures to take data for forming the stem.
Figure 13:
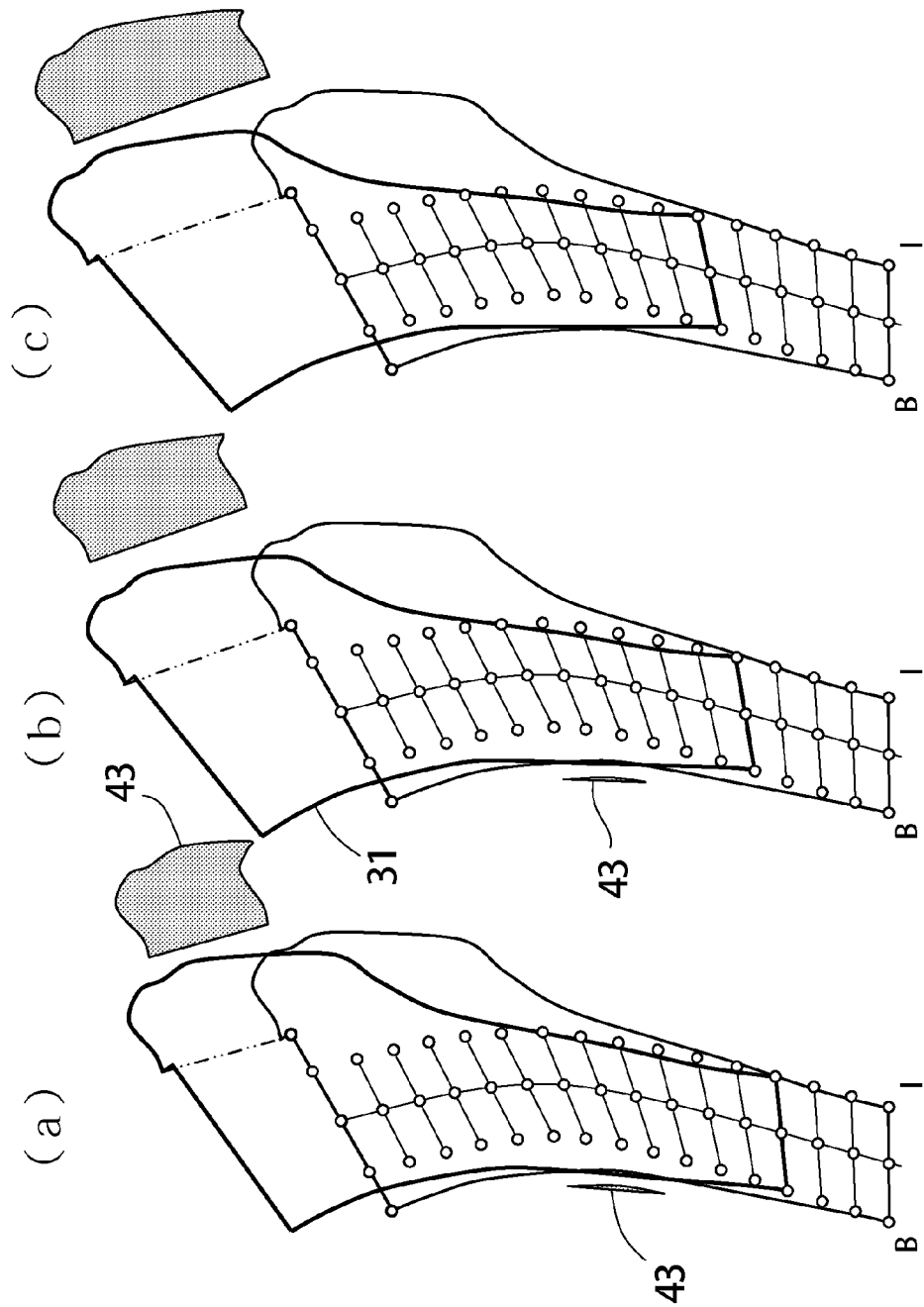
[FIG. 13]: a series of figures to take data for forming the stem after that of FIG. 12.
Figure 14:
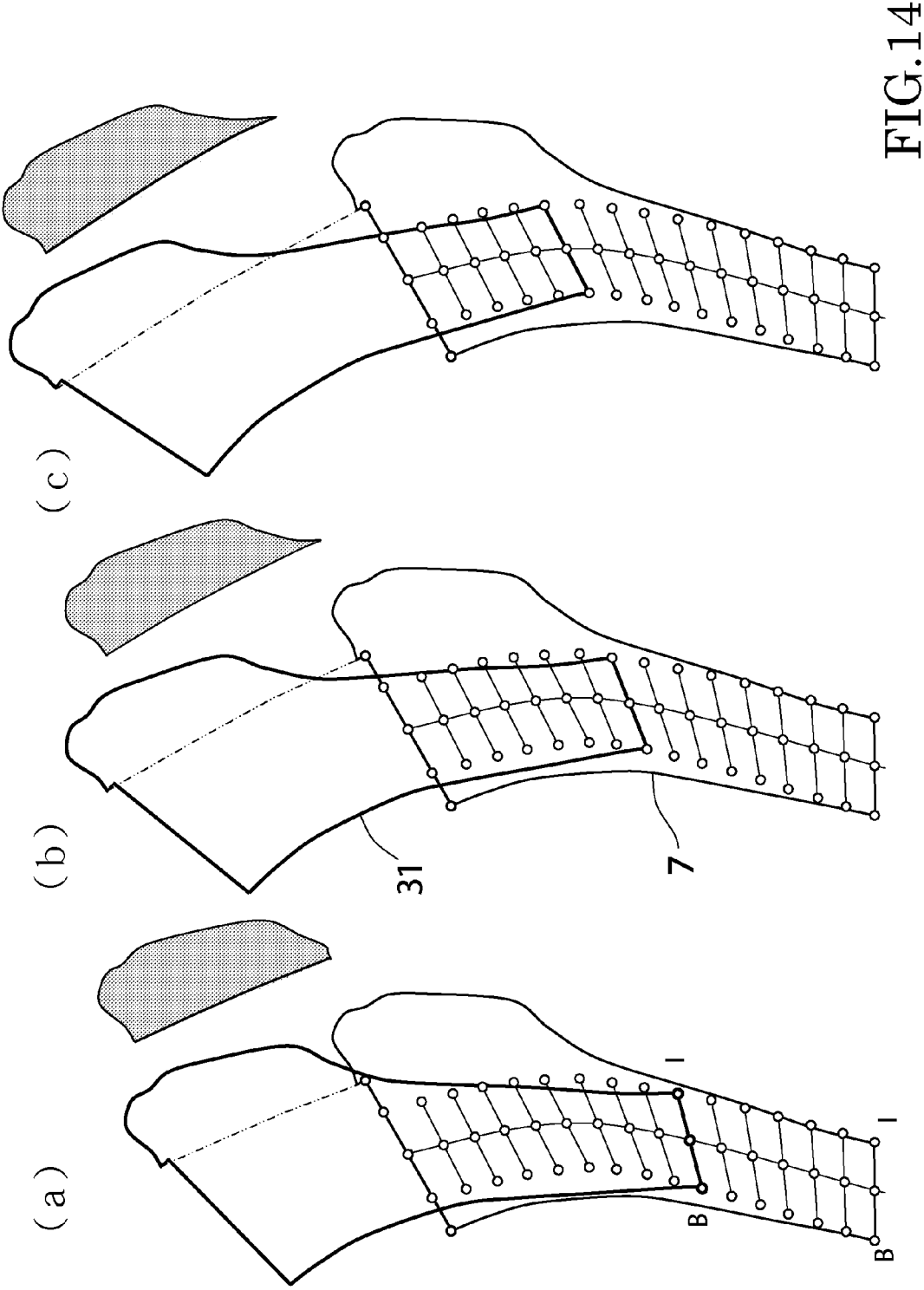
[FIG. 14]: a series of figures to take data for forming the stem after that of FIG. 13.

The figures from 12 to 14 show the state that the imaginary three dimensional stem 31 is pulled by one step out of the imaginary three dimensional deep hollow 7 by applying the transitional values 41 of occupied position to the imaginary three dimensional stem 31, but shown two-dimensionally in order to simplify it. FIG. 12(a) shows the imaginary three dimensional deep hollow 7 obtained from the data of the limitary thickness of the bonny tissue determined on the base of the threshold value of bony density, the suitable length of the stem for the patient, and the imaginary three dimensional stem 31 obtained from the positions of the epiphysis opening and diaphysis opening. FIG. 12(b) shows the imaginary three dimensional stem 31 having the same shape as the shape of the imaginary three dimensional deep hollow 7. FIG. 12(c) is the figure of the imaginary three dimensional stem 31 raised by one step in the imaginary three dimensional deep hollow 7 by applying the transitional values of the occupied position to the imaginary stem 31. Thus the imaginary three dimensional stem 31 is moved in the imaginary three dimensional deep hollow 7 successively to the next step, but it is inevitable for them to interfere with each other. As shown in FIG. 12(c) to FIG. 13(b), a part of the imaginary three dimensional stem 31 is off from the imaginary three dimensional deep hollow 7 (see the numeral 43), although it is just on calculation.

Figure 15:
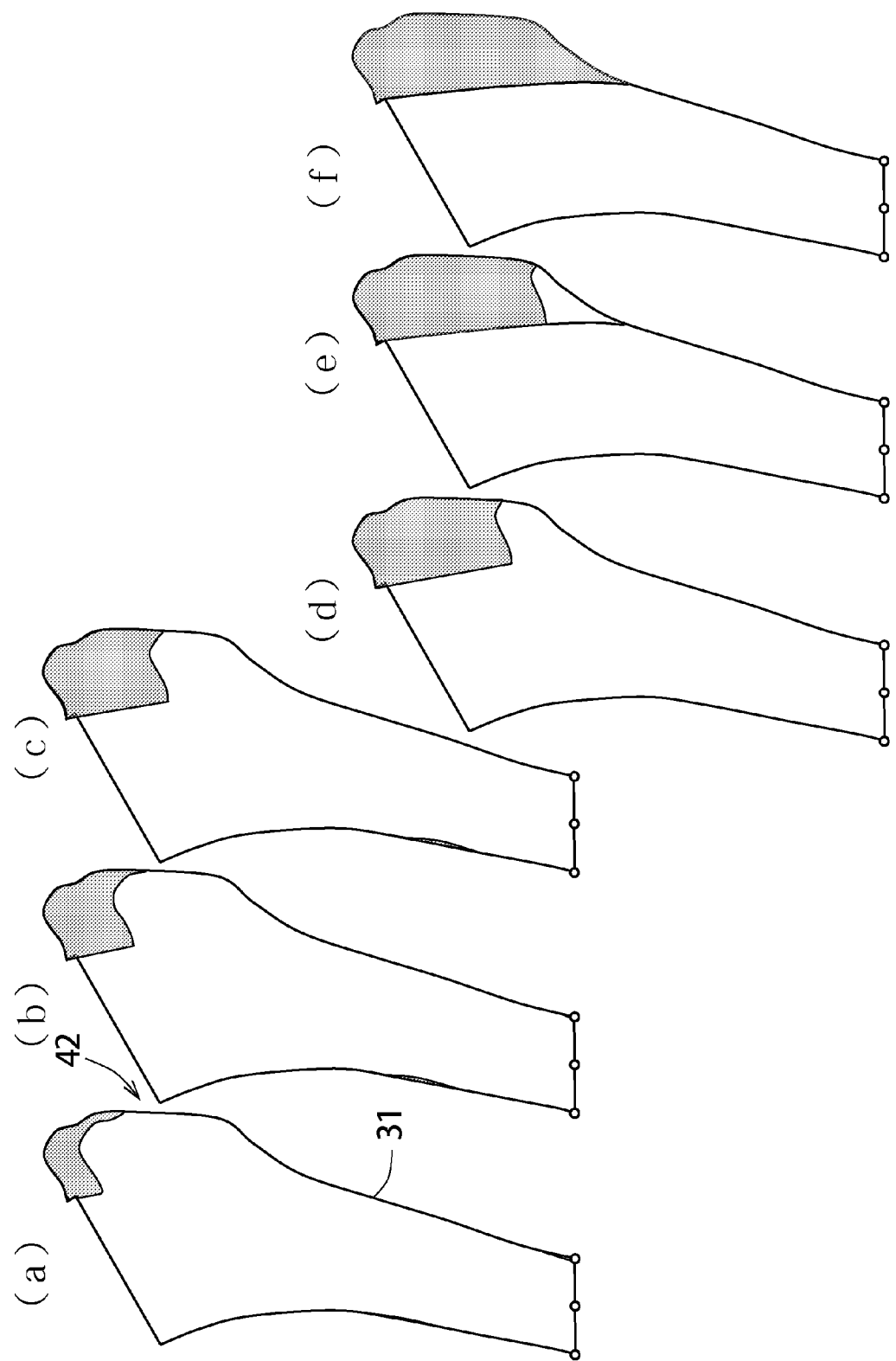
[FIG. 15]: a diagram of the way to process the stem.

In FIG. 15 there are the six steps lined up, from FIG. 12(c) to FIG. 13(c) and FIG. 14(c), which show all the portions to be removed from the imaginary three dimensional stem 31. The shape of the imaginary three dimensional stem is calculated whose interference portions are entirely removed on the basis of the data in storage, and the reference stem is obtain whose final shape is inscribed to the supposed inner surface of shape for the purpose of by smoothing the outer surface of shape of the imaginary three dimensional stem. The thick solid lines drawn in FIG. 16(a) show the shape of the imaginary three dimensional stem 31, from which the interference portions are removed. The removed portion of the greater trochanter 42 is noticeable but it is obvious from FIG. 15 that both the body 32 and nose 31 are removed a little. FIG. 16(b) shows the reference stem 44 having the final shape. FIG. 16(c) shows the shape of the finished stem 45 having a neck for holding a spherical head, a shoulder and a nose cap. The direction and the length of the neck are determined in response to the position of the socket fixed on the pelvis.

Figure 16:
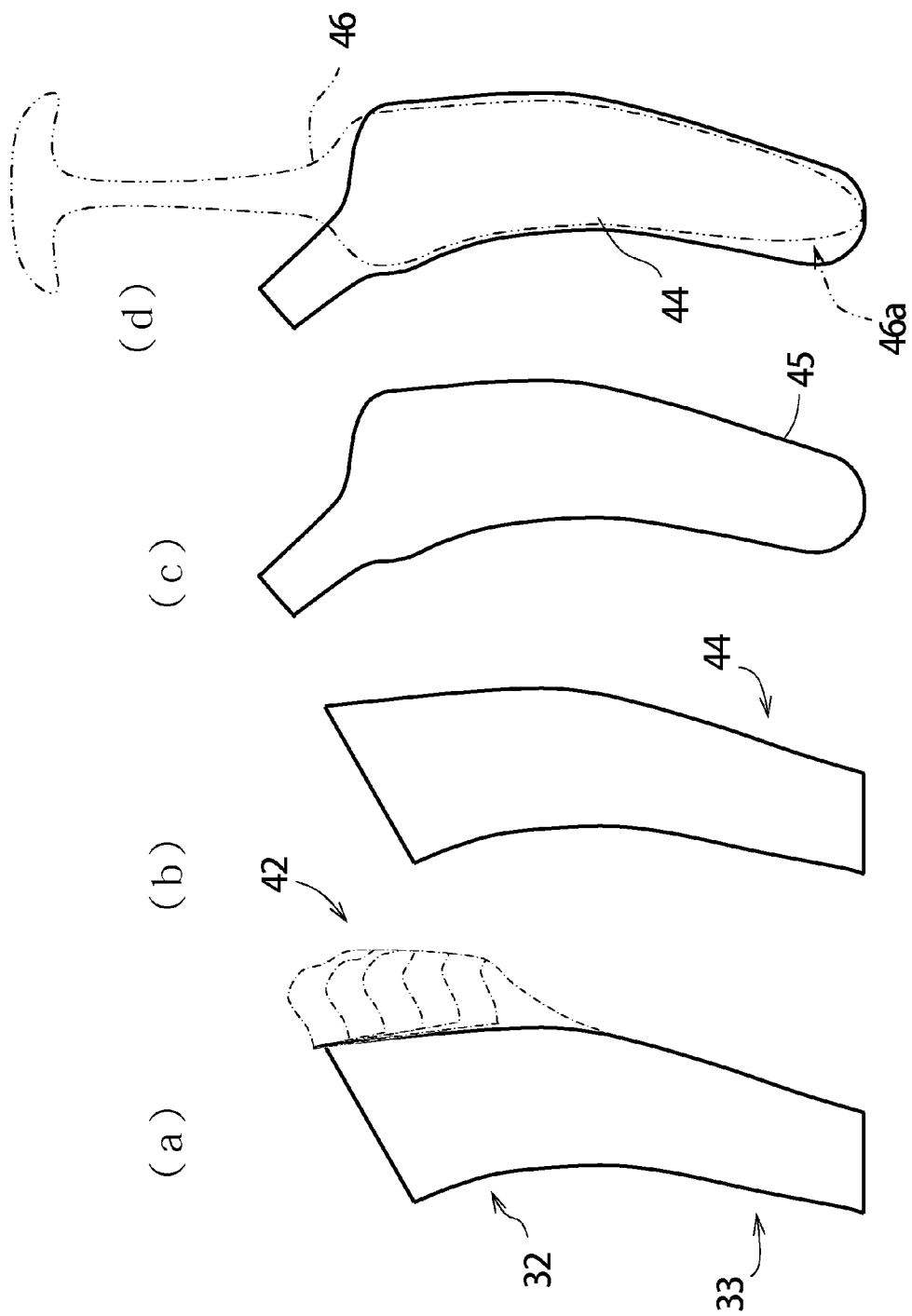
[FIG. 16]: a diagram of the way to decide the shape of the stem.

In FIG. 16 (d), a rasp 46 is shown which is a reproduction of the finished stem 45, whose body is made so as to be slightly small and the nose 46a is made so as to be thin, which enables the rasp to easily advance into the spongiosa, and moreover, the adhesion and the stability of the stem may be promoted by the last pushing and tapping it into the deep hollow because some spongiosa is left in the deep hollow from which the rasp has been removed.

Calculating the data on the positions and postures of the reference stem 44 having the final shape while putting the stem gradually into the imaginary three dimensional deep hollow 7 by taking the reverse steps of the series of steps mentioned above, visually learning the positions and postures of the stem beforehand by means of a series of pictures 47 of inserting the stem shown in FIG. 1(a), and making plastic models of the stem and the femur on the basis of the data, help the surgeon to make sure the process of implanting the stem with the sense of touch before the surgical operation. The fact that the shape of the rasp is nearly the same as that of the stem will get rid of his uneasiness in handling the rasp, and the duration for the surgery may be shortened.

Figure 24:
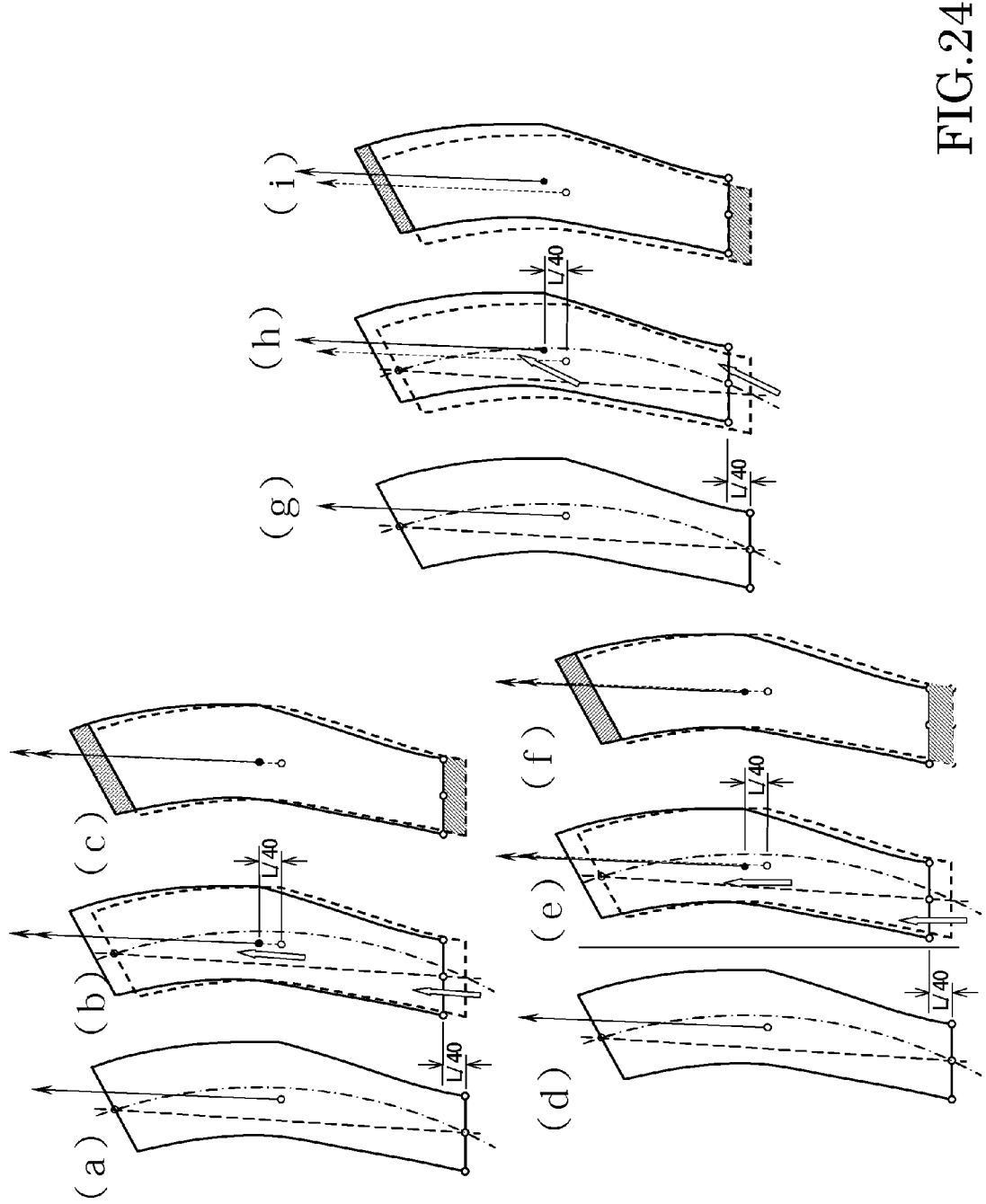
[FIG. 24]: a diagram of the way to move the stem.

On pulling the imaginary three dimensional stem 31 out of the imaginary three dimensional deep hollow 7, the course to raise the stem may be parallel to the line from the center of figure of the epiphysis opening to the center of figure of the diaphysis opening, as shown in FIG. 24 (a), (b) and (c), or may be absolute vertical as shown in (d), (e) and (f), or may be along the reference arc as shown in (g), (h) and (i). The posture of the stem is automatically adjusted when the stem deviates from the course, since it is controlled by the principal axes of inertia.

Figure 17:
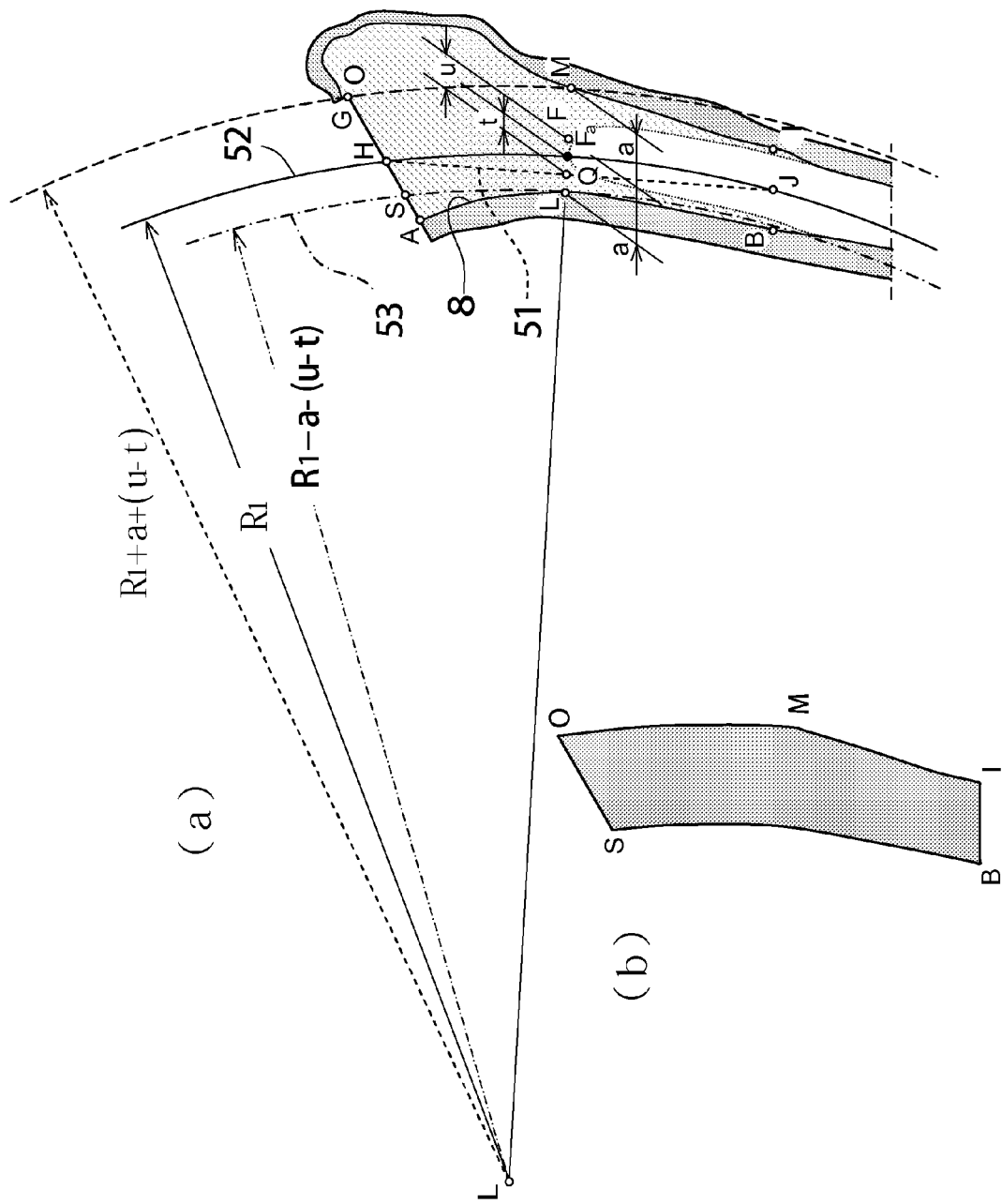
[FIG. 17]: an explanatory diagram to set the co-ordinates for forming a deep hollow in a femur.

The above is with regard to the method of deciding the shape of the stem detected by using the provisional three dimensional reference stem 18 which is made of the pattern 16 of provisional deep hollow on the plane including the crotch and counter-crotch side lines and the pattern 17 of provisional deep hollow on the plane including the anterior and posterior side lines made on the basis of the reference arc 19 on the plane including the crotch and counter-crotch side lines and the reference arc 20 on the plane including the anterior and posterior side lines which pass through the reference point F in the lateral direction and the reference point Fr in the direction perpendicular to lateral direction shown in FIG. 4 and FIG. 5 respectively. However, as shown in FIG. 17, another reference stem may be made by substituting the point Fa for the reference point F in the lateral direction mentioned above, which is taken more inward from the reference point F. It is clear from FIG. 17 that the curvature of the arc passing through the point Fa is small.

More particularly, the alternative reference point Fa in the lateral direction is taken between the reference point F in the lateral direction and a straight segment 51 connecting the center H of figure of the epiphysis opening 13 and the center J of figure of the diaphysis opening 14. And the alternative reference point in the direction perpendicular to lateral direction is taken between the straight segment 51 and the reference point Fr in the direction perpendicular to lateral direction as well. The alternative reference point Fa in the lateral direction is regarded as the reference point F in the lateral direction, and the alternative reference point in the direction perpendicular to lateral direction is regarded as the reference point Fr, so that the alternative reference arc 52 on the plane including the crotch and counter-crotch side lines and the alternative reference arc on the plane including the anterior and posterior side lines line can be made, which have different curvatures from those of reference arc 19 on the plane including the crotch and counter-crotch side lines and the reference arc 20 on the plane including the anterior and posterior side lines, in the same process mentioned above. The process of making the provisional three dimensional reference stem including these curvatures is the same as that of making the provisional three dimensional reference stem 18. Calculating the occupied positions every step after that, calculating the interference portions of the imaginary three dimensional stem 31 and the imaginary three dimensional deep hollow by using the occupied positions, and putting them in storage, enable the final shape of the alternative stem to be obtained as a substitute for the reference stem 44.

The alternative stem is available when the surgeon needs another stem having a gentle bend, for the stem made on the basis of the reference point F in the lateral direction bends too sharp to insert into the deep hollow. In the case that the alternative three dimensional reference stem is obtained, there is no need to use the pseudo-arc 21 regarding as the crotch side line and the pseudo-arc 22 regarding as anterior side line, for curvature thereof tends to be small. Therefore, the alternative small arc 53 on the plane including the crotch and counter-crotch side lines which is concentric with the alternative reference arc 52 on the plane including the crotch and counter-crotch side lines, may have a radius which is shorter than the radius of the alternative reference arc 52 on the plane including the crotch and counter-crotch side lines but longer than the distance to the end point A of the epiphysis on the crotch side line 8.

Figure 18:
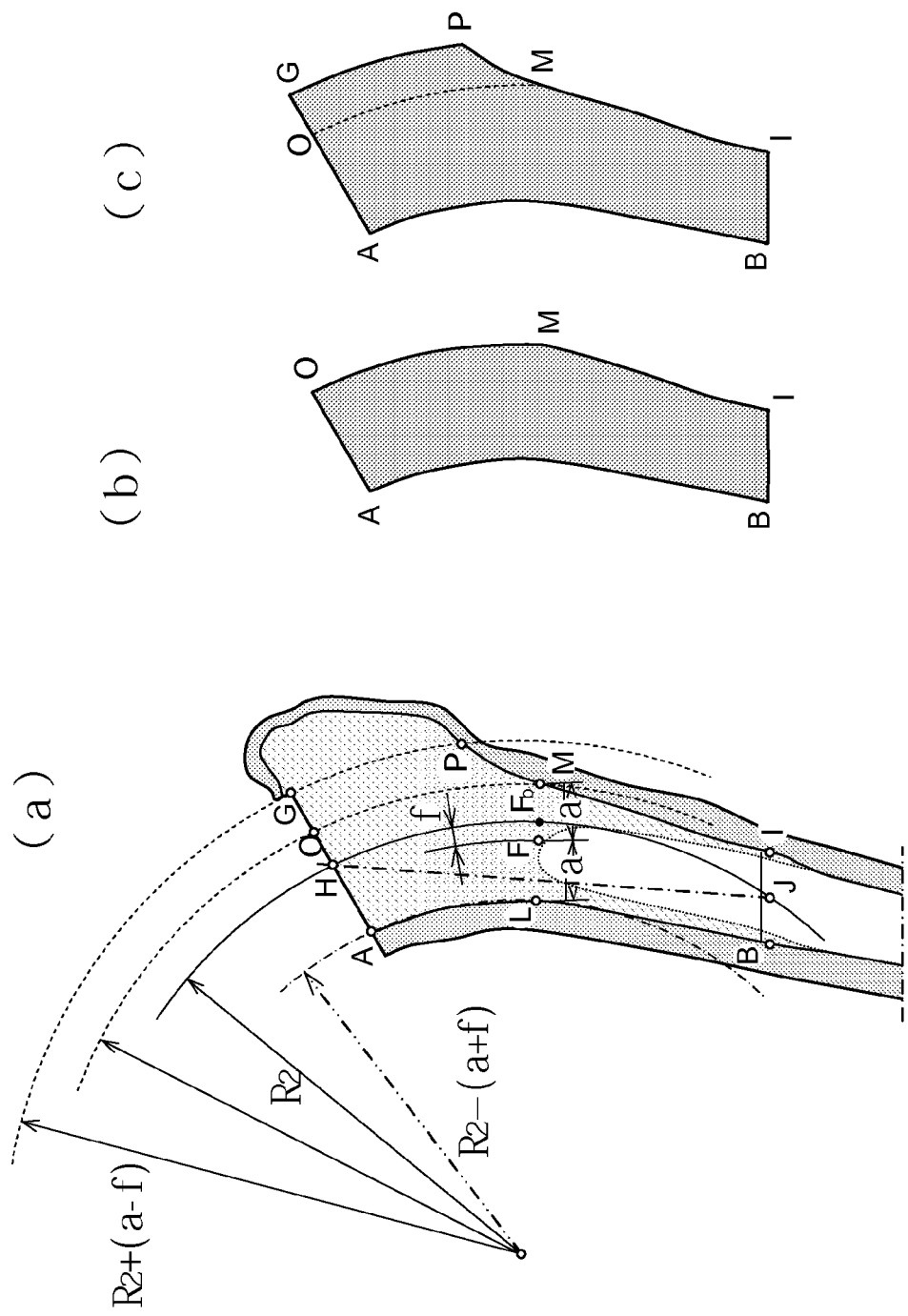
[FIG. 18]: an explanatory diagram to set the co-ordinates for forming a deep hollow in a femur.
Figure 19:
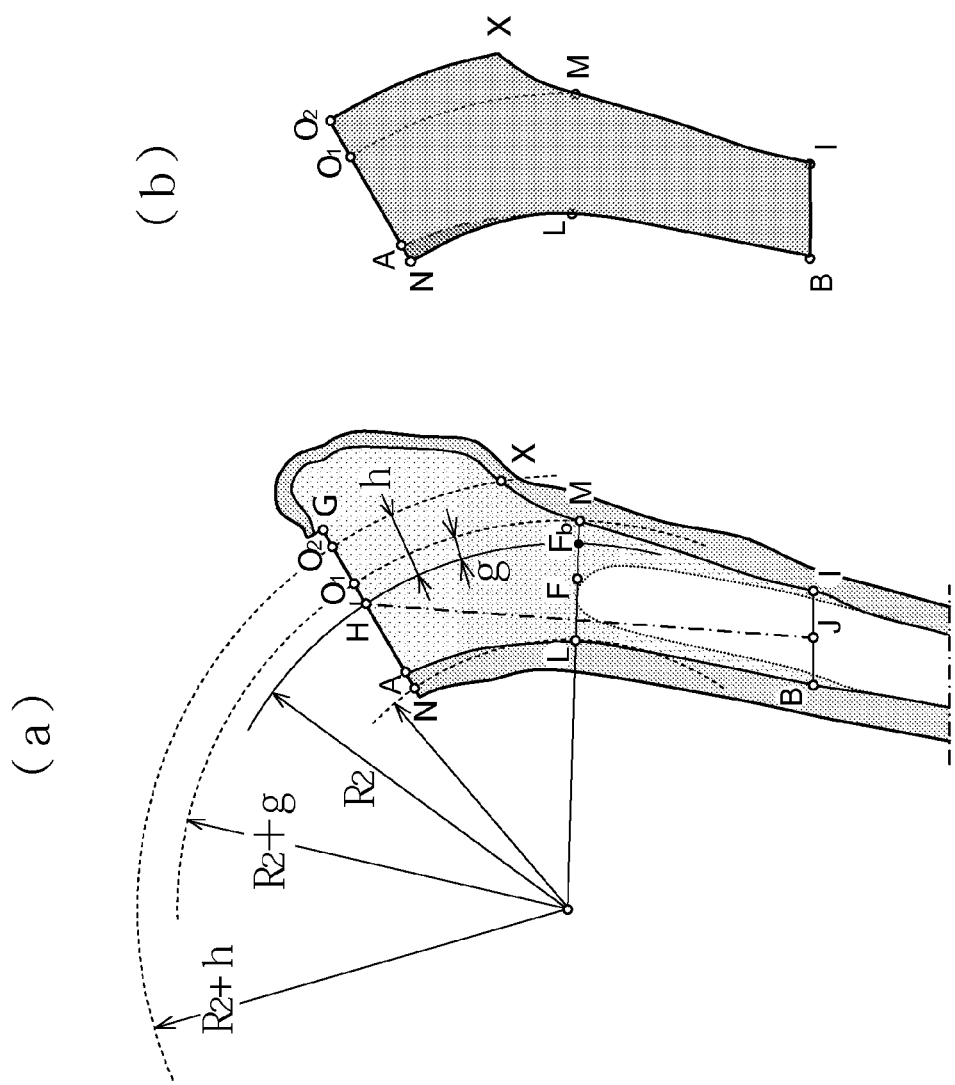
[FIG. 19]: an explanatory diagram to set the co-ordinates for forming a deep hollow in a femur.

Incidentally, in the case of FIG. 18 and FIG. 19, the alternative reference point Fb in the lateral direction is taken in the opposite position of the reference point F in the lateral direction. In this case, the stem may have a big curvature which is far beyond the curvature of the femur having the alternative reference arc 52 on the plane including the crotch and counter-crotch side lines and the alternative reference arc on the plane including the anterior and posterior side lines, making the alternative stem not symmetric with the deep hollow, resulting in having the stem which is hard for the surgeon to handle. Accordingly in order to implant the alternative stem into the deep hollow successfully, the curvature given by the alternative reference point ought to be limited to such an extent that it would not exceed the curvature given by the reference point F in the lateral direction. The stem shown in FIG. 19, is too bent to implant in the deep hollow.

Figure 20:
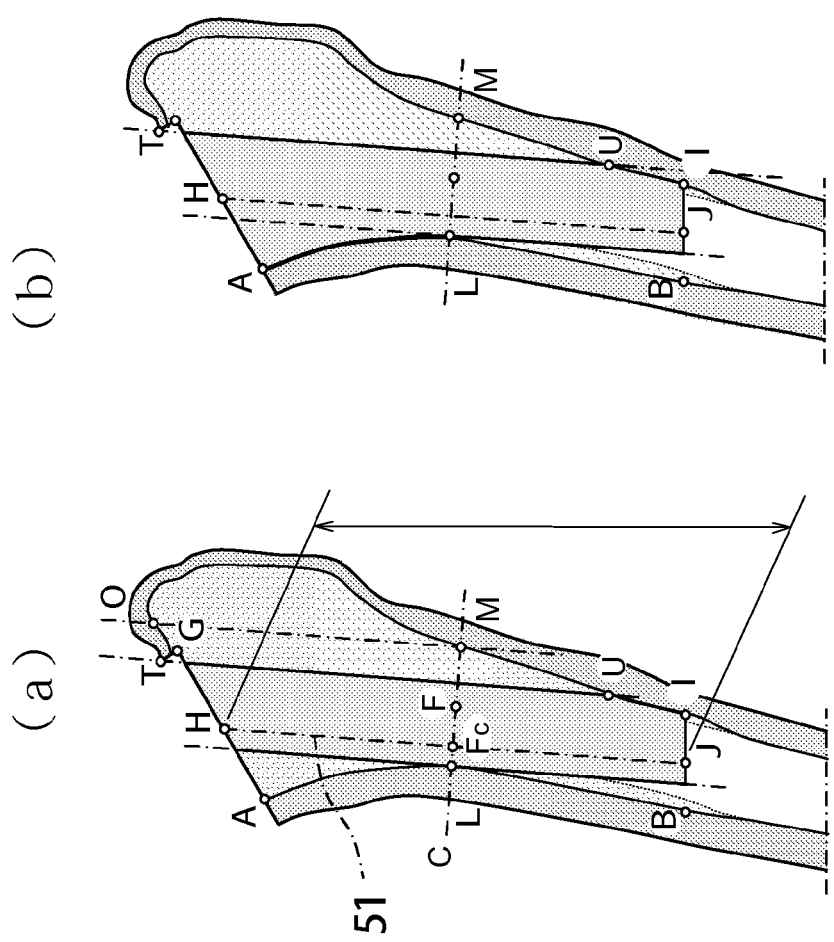
[FIG. 20]: an explanatory diagram to set the co-ordinates for forming a deep hollow in a femur.
Figure 21:
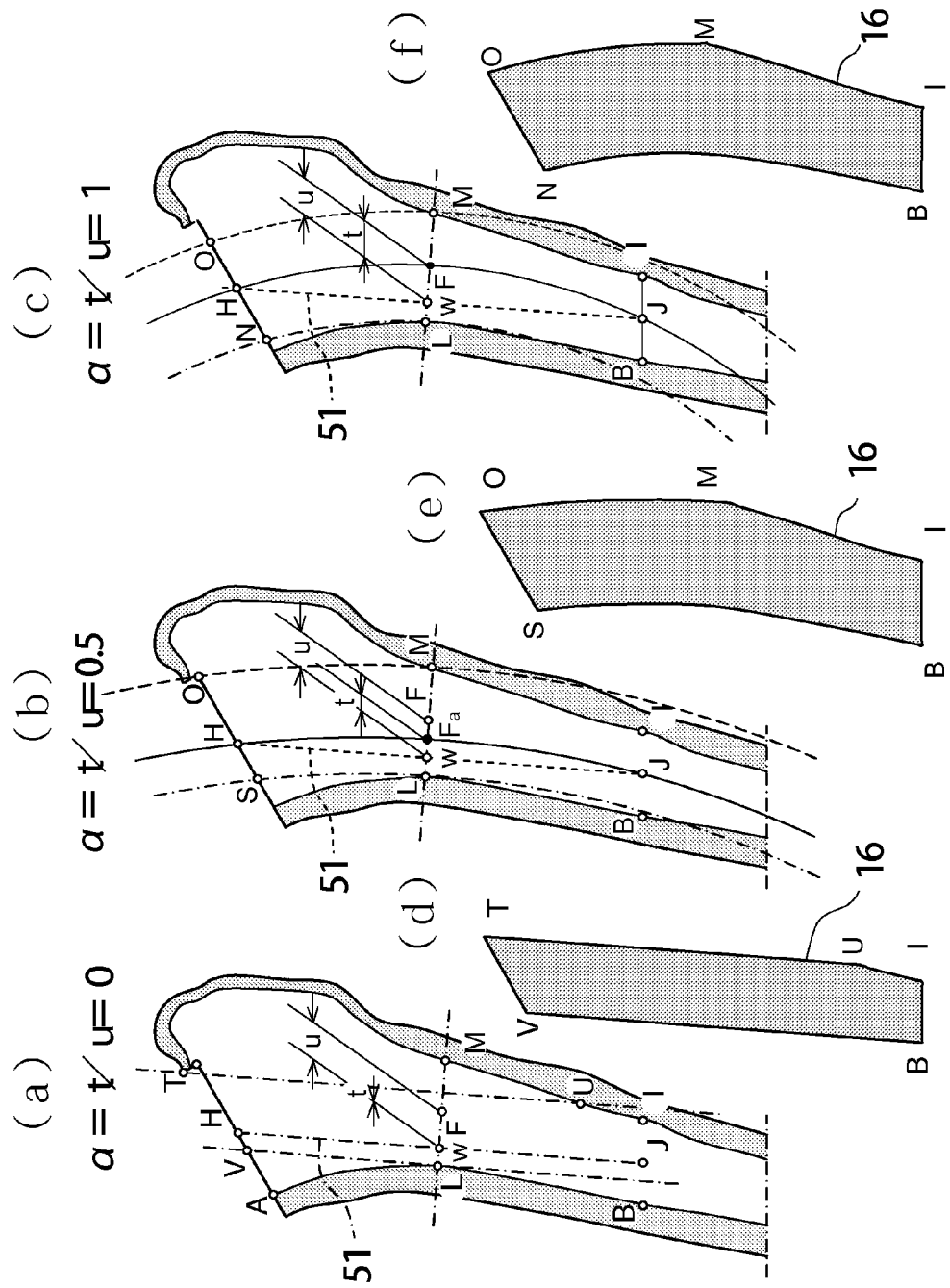
[FIG. 21]: an explanatory diagram to set the co-ordinates for forming a deep hollow in a femur.
Figure 22:
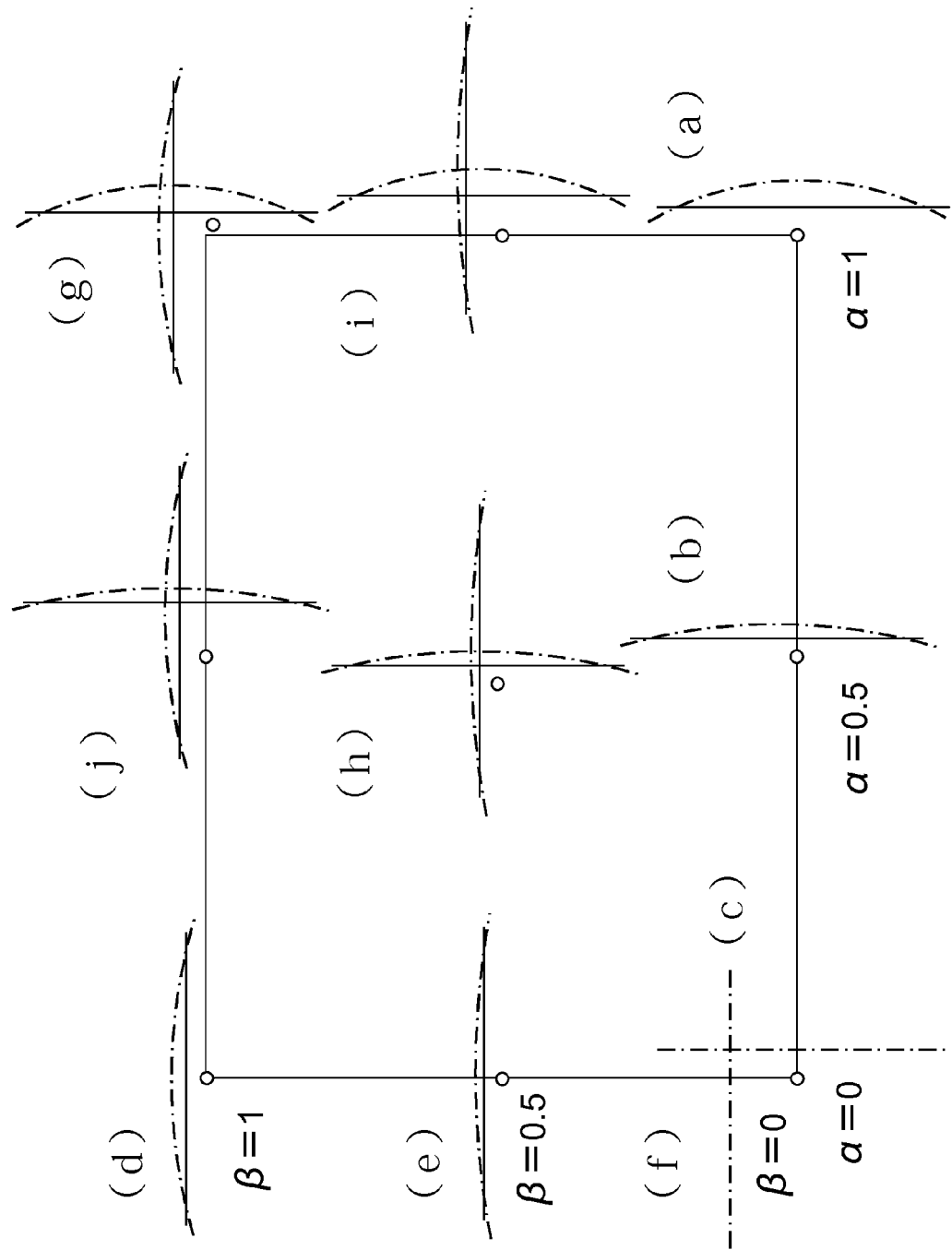
[FIG. 22]: a diagram of the stems having different curvatures.

When the alternative reference point Fc in the lateral direction is lain on the straight segment 51 as shown in FIG. 20(a), the three points for forming the reference arc on the plane including the crotch and counter-crotch side lines will determine a straight line, whose curvature is consequently zero, that is, the stem has a straight shape as illustrated in FIG. 20(a). Being made like (b) in FIG. 20, this is the stem as mentioned in FIG. 26 (c) of the Background Art. FIG. 21 shows how the shape of the pattern 16 of provisional deep hollow on the plane including the crotch and counter-crotch side lines may change in response to the difference between the alternative reference arc on the plane including the crotch and counter-crotch side lines and the reference arc on the plane including the crotch and counter-crotch side lines. In this figure, the ratio of the distance from the straight segment 51 to alternative reference point Fa in the lateral direction taken between the straight segment 51 and the reference point F in the lateral direction to the distance from the straight segment 51 to the reference point F in the lateral direction, is defined by bending ratio $\alpha$ on the plane along the lateral direction, and the ratio of the distance from the straight segment 51 to the alternative reference point in the direction perpendicular to the lateral direction taken between the straight segment 51 and the reference point Fr (see FIG. 7) in the direction perpendicular to the lateral direction to the distance from the straight segment to the reference point Fr in the direction perpendicular to the lateral direction, is defined by bending ratio $\beta$ on the plane along the direction perpendicular to the lateral direction.

case of $\alpha=0$ and $\beta=0$
case of $\alpha=0.5$ and $\beta=0$
case of $\alpha=1$ and $\beta=0$
case of $\alpha=0$ and $\beta=0.5$
case of $\alpha=0.5$ and $\beta=0.5$
case of $\alpha=1$ and $\beta=0.5$
case of $\alpha=0$ and $\beta=1$
case of $\alpha=0.5$ and $\beta=1$
case of $\alpha=1$ and $\beta=1$ With regard to the nine cases mentioned above, the transition in the position and posture of the imaginary rasp can be seen in FIG. 22, which has the same shape and size as the reference stem 44 and the alternative stem, when being gradually pushed into the imaginary three dimensional deep hollow. In the case of (f), the left side of the bottom of the figure, when $\alpha=0$ and $\beta=0$, the stem is straight, having the smallest curvature. In the case of (g), the right side of the top of the figure, when $\alpha=1$ and $\beta=1$, the stem has the biggest curvature. In the cases of the rest, the stem has moderate curvatures between (f) and (g). Seeing the series of pictures of the positions and postures of the stems of these nine cases while pulling the stem out of the deep hollow, see FIG. 1(a) for instance, helps the surgeon to find out some suitable stems close to his plans of handling, or to select the very suitable one among them. Although he finds a fairly good stem, he hopes to see the case marked with the black dot; $\alpha=0.75$ and $\beta=0.75$, it is naturally possible to calculate again. The surgeon may select the stem which is very close to his plans of handling stem, or may have a re-alternative stem which gives a good agreement with his plans by proposing another curvature. Thus, many kinds of stem can be rapidly and easily limited to some usable stems. Even if he hopes a very special stem, as far as the bending ratios thereof can be given in terms of $\alpha$ and $\beta$, the stem can be calculated in the method as explained above. The re-alternative stem can be shown in less than 20 or 30 minutes when the stem needed is only one, since there is no need to make a fresh start of calculating.

Figure 25:
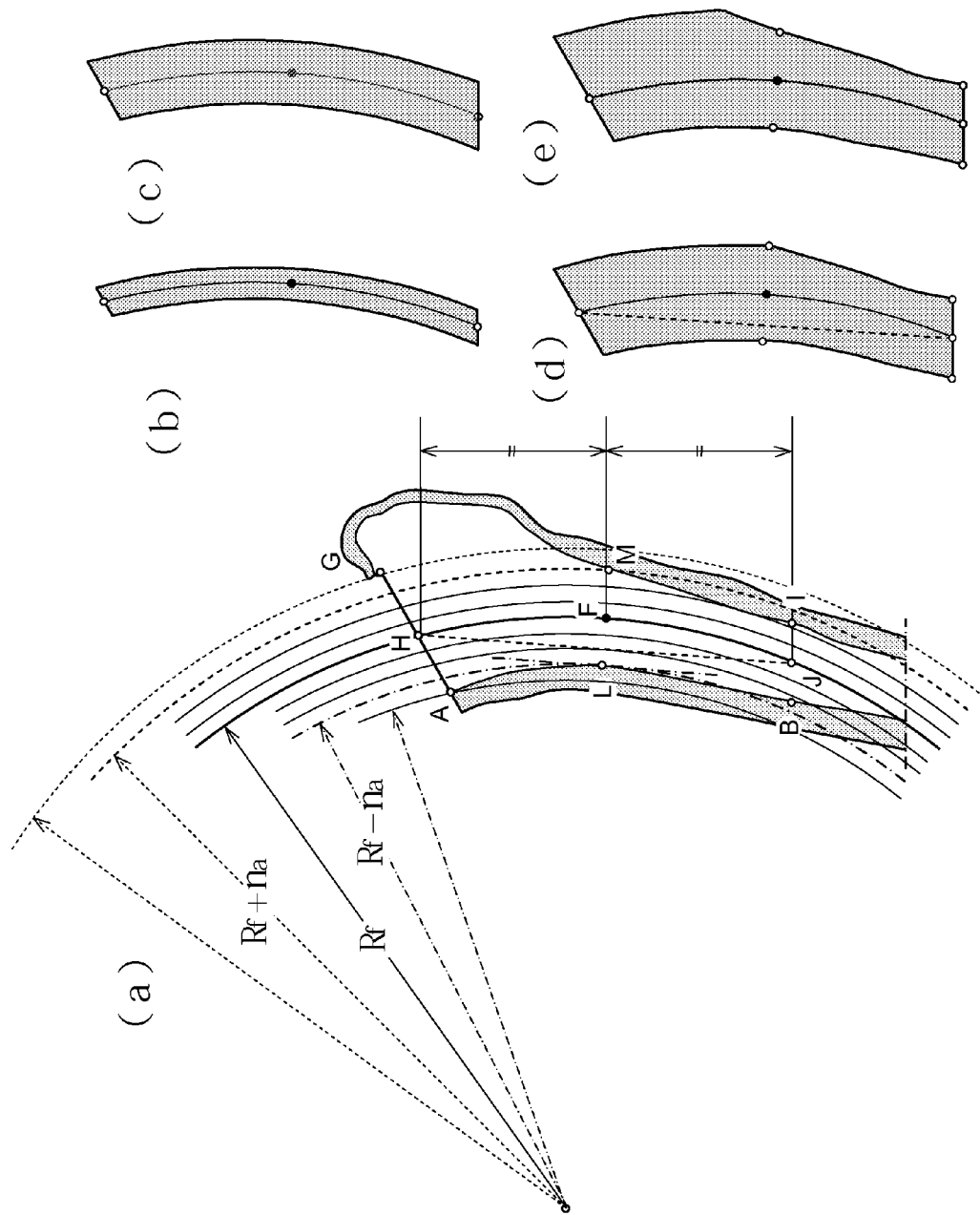
[FIG. 25]: an explanatory diagram to set the co-ordinates for forming a deep hollow in a femur.

In order to make the provisional deep hollow on the plane including the crotch and counter-crotch side lines, for instance, the small arc and the large arc are applied thereto which are concentric with the reference arc, however, other arcs shown in FIG. 25 may be selected. At least the reference arc has to pass through the center H of figure of the epiphysis opening 13 and the center J of figure of the diaphysis opening 14, but any arc of (b) to (e) in FIG. 25 is usable as far as they are concentric with the reference arc.

As mentioned above, the pattern of provisional deep hollow on the plane including the crotch and counter-crotch side lines and the pattern of provisional deep hollow on the plane including the anterior and posterior side lines are obtained by substituting the imaginary three dimensional deep hollow whose cross section has regular curvature for the deep hollow formed in the femur to have a surgery, whose cross section has irregular curvature, thereby, the provisional three dimensional reference stem is obtained, which consist of a body formed by a body surrounded by four side planes, i.e., patterns mentioned above, and nose formed by the corresponding part of the patient's deep hollow, and the provisional three dimensional reference deep hollow which has having the same shape as the reference stem is also obtained to substitute for the imaginary three dimensional deep hollow. The calculation displaying the high accuracy of overlapping the provisional three dimensional reference stem on the provisional three dimensional reference deep hollow specifies the combination of the positions and postures of the reference stem by coinciding its principal axes of inertial with that of the reference deep hollow by one step while the stem is pulled out of the reference deep hollow to only one combination of them, realizing the calculating for designing the provisional three dimensional reference stem with such a specified curvature. The positions and the postures of the provisional three dimensional reference stem, which have already obtained by the calculation mentioned above, are applied to the imaginary three dimensional stem having the same shape as the imaginary three dimensional deep hollow to obtain the portions interfered with the imaginary three dimensional deep hollow while the stem is pulled out of the imaginary three dimensional deep hollow and to remove the interference portion from the reference stem, resulting in achieving the high rate of Fill at the body of the reference stem and the high rate of Fill at the nose, though the imaginary three dimensional deep hollow is used in the calculation instead of the actual deep hollow.

The invention claimed is:

1. A method of determining a shape of an artificial cementless hip prosthesis stem, adapted to be implanted into a deep hollow extending from an epiphysis of a femur to a diaphysis, so as to be gradually united with the femur by bone growth, comprising;

detecting a limitary thickness of a bony tissue of each part of the femur destined to receive the prosthesis stem, which is necessary for forming a wall of the deep hollow, by applying a threshold bold density value to three dimensional graphics data based on computed tomography (CT) data and magnetic resonance imaging (MRI) data obtained from the femur, calculating a shape of an imaginary three dimensional deep hollow extending to a medullary cavity, which is formed inside the bony tissue, and also calculating coordinates of a crotch side line and a counter-crotch side line for regulating a shape of a lateral section of the deep hollow, and coordinates of an anterior side line and a posterior side line for regulating a shape of a section perpendicular to the lateral section of the deep hollow;

calculating a shape of an epiphysis opening of the imaginary three dimensional deep hollow and a position of a center of a figure of the shape, from a position and an angle of the epiphysis opening determined based on a predetermined reference line which is parallel to a longitudinal direction of the femur, and also calculating a shape of a diaphysis opening of the imaginary three dimensional deep hollow and a position of a center of a figure of the shape, from a length of the stem to be applied to the femur and an angle of the diaphysis opening;

calculating a reference arc on a plane including the crotch-side line and the counter-crotch line which passes through the center of the figure of the epiphysis opening, the center of the figure of the diaphysis opening, and a reference point in a lateral direction, which lies halfway between the two centers of the two figures, and a distance to said crotch side line corresponding to a distance to the counter-crotch side line;

obtaining a pattern of a provisional deep hollow on the plane including the crotch and counter-crotch side lines, which is formed inside said imaginary three dimensional deep hollow surrounded by a small arc on the plane including the crotch and counter-crotch side lines which is concentric with the reference arc on the plane including the crotch and counter-crotch side lines and has a radius which is shorter than a radius of the reference arc and longer than a distance to an end point of the epiphysis lying on said crotch side line, a large arc on the plane including the crotch and counter-crotch side lines which is concentric with said reference arc and has a radius which is longer than the radius of said reference arc and shorter than the distance to the end point of the epiphysis lying on said counter-crotch side line, the crotch side line which extends from a terminal point of the small arc where said small arc intersects the crotch side line to an end point of the diaphysis lying on the crotch side line, and the counter-crotch side line which extends from a terminal point of the large arc where said large arc intersects the counter-crotch side line to an end point of the diaphysis lying on the counter-crotch side line;

calculating a reference arc on a plane including the anterior and posterior side lines, the reference arc passing through the center of the figure of the epiphysis opening, the center of the figure of the diaphysis opening, and a reference point in a direction perpendicular to a lateral direction, which lies halfway between the two centers of the two figures, and a distance to said anterior side line corresponding to a distance to the posterior side line, obtaining a pattern of the provisional deep hollow on the plane including the anterior and posterior side lines, which is formed inside said imaginary three dimensional deep hollow surrounded by a small arc on the plane including the anterior and posterior side lines which is concentric with the reference arc on the plane including the anterior and posterior side lines and has a radius which is shorter than a radius of the reference arc and longer than a distance to an end point of the epiphysis lying on said anterior side line, a large arc on the plane including the anterior and posterior side lines which is concentric with said reference arc and has a radius which is longer than a radius of said reference arc and shorter than a distance to an end point of the epiphysis lying on said posterior side line, the anterior side line extending from a terminal point of the small arc where said small arc intersects the anterior side line to an end point of the diaphysis lying on the anterior side line, and the posterior side line extending from a terminal point of the large arc where said large arc intersects the posterior side line to an end point of the diaphysis on the posterior side line;

making a provisional three dimensional reference stem containing the reference arc on the plane including the crotch and counter-crotch side lines and the reference arc on the plane including the anterior and posterior side lines, which consists of a body surrounded by four side planes formed by arranging said patterns of the provisional deep hollow on the plane including the crotch and counter-crotch side lines on the anterior side line and the posterior side line respectively so as to face each other and said patterns of the provisional deep hollow on the plane including the anterior and posterior side lines on the crotch side line and the counter-crotch side line respectively so as to face each other, and a quasi-circular cylinder having a same shape as said imaginary three dimensional deep hollow corresponding to a region extending from each terminal point of the small arc and the large arc of the body surrounded by the four planes to the diaphysis opening;

making a provisional three dimensional reference deep hollow which has a same shape as said provisional three dimensional reference stem, in order to calculate a position and a posture of the provisional three dimensional reference stem on each step as the stem is gradually pulled out of the deep hollow, obtaining a residual portion of the provisional three dimensional reference deep hollow whose diaphysis portion is removed, where the deep hollow does not overlap every step of the stem, calculating a center of gravity and a principal axis of inertia thereof, and obtaining a residual portion of the provisional three dimensional reference stem whose epiphysis portion is removed, where the stem does not overlap every step of the deep hollow, calculating a center of gravity and a principal axis of inertia thereof, shifting the center of gravity of the residual portion of the provisional three dimensional reference stem to the principal axis of the residual portion of the deep hollow in a direction for pulling the stem with a condition that a posture of the stem is kept in the step, rotating the residual portion of the provisional three dimensional reference stem around the center of gravity shifted in a last step so as to coincide the principal axis of inertia of the residual portion of provisional three dimensional reference stem in the direction of pulling the stem with the principal axis of inertia of the residual portion of provisional three dimensional reference deep hollow in the direction of pulling the stem, calculating positions of the end points of the diaphysis lying on the crotch side line and the anterior side line of the residual portion of the provisional three dimensional reference stem, and the end points of the diaphysis lying on the counter-crotch side line and the posterior side line which occupy every step;

making an imaginary three dimensional stem which has a same shape as said imaginary three dimensional deep hollow, moving the imaginary three dimensional stem in the imaginary three dimensional deep hollow by applying transitional values to said occupied positions to the imaginary stem, calculating interference portions where the imaginary three dimensional stem is disturbed when moving in the imaginary three dimensional deep hollow while the stem is pulled out of the deep hollow and saving the calculated interference portions as data;

calculating an outer surface of the shape of the imaginary three dimensional stem whose interference portions are entirely removed based on the stored data, obtaining a reference stem whose final shape is inscribed to an inner surface of the shape for the purpose of smoothing an outer surface of the shape of the imaginary three dimensional stem, taking an alternative reference point in a lateral direction on a region between a straight segment from the center of the figure of the epiphysis opening to the center of the figure of the diaphysis opening and said reference point in the lateral direction, taking an alternative reference point in a direction perpendicular to a lateral direction on a region between said straight segment and said reference point in a direction perpendicular to the lateral direction, the alternative reference point in the lateral direction being regarded as the reference point in the lateral direction, and the alternative reference point in the direction perpendicular to the lateral direction being regarded as the reference point in the direction perpendicular to the lateral direction, obtaining an alternative provisional three dimensional reference stem having an alternative reference arc on the plane including the crotch and counter-crotch side lines whose curvature is different from that of the reference arc on the plane including the crotch and counter-crotch lines and an alternative reference arc on the plane including the anterior and posterior side lines whose curvature is different from that of the reference arc on the plane including the anterior and posterior side lines, calculating said occupied positions for every step, obtaining a final shape of the alternative stem by following the procedure for calculating the interference portions of the stem where the imaginary three dimensional stem is disturbed when moving in the imaginary three dimensional deep hollow by using the occupied position, and storing the data; and, computing data on positions and postures of the reference stem and the alternative stem which have said final shape while putting these stems gradually into said imaginary three dimensional deep hollow, by following the above steps in reverse.

2. The method of determining the shape of an artificial cement-less hip prosthesis stem according to claim 1, wherein in the step where the provisional three dimensional reference stem is gradually pulled out of the provisional three dimensional reference deep hollow, the method further comprises moving the center of gravity of said residual portion of the provisional three dimensional reference stem along a line from said center of gravity of the residual portion of the provisional three dimensional reference stem to said center of the figure of the epiphysis opening of said imaginary three dimensional deep hollow with a condition that a posture of the stem at every step is kept, calculating occupied positions of the end points of the diaphysis lying on the crotch side line and the anterior side line of the residual portion of the provisional three dimensional reference stem and of the end points of the diaphysis lying on the counter-crotch side line and the posterior side line.

3. The method of determining the shape of an artificial cement-less hip prosthesis stem according to claim 2, wherein:

the radius of said small arc on the plane including the crotch and counter-crotch side lines is equal to a radius of a pseudo-arc regarded as the crotch side line which passes through the end point of the diaphysis and the end point of the epiphysis lying on the crotch side line of said imaginary three dimensional deep hollow, and a point most protruded in a lateral direction on the crotch side line, where a line parallel to a straight line passing through these two end points contacts the crotch side line, and the radius of said small arc on the plane including the anterior and posterior side lines is equal to a radius of a pseudo-arc regarded as the anterior side line which passes through the end point of the diaphysis and the end point of the epiphysis lying on the anterior side line of said imaginary three dimensional deep hollow, and a point most protruded in a direction perpendicular to the lateral direction on the anterior side line, where a line parallel to a straight line passing through these two end points contacts the anterior side line.

4. The method of determining the shape of an artificial cement-less hip prosthesis stem according to claim 2, wherein:

the radius of said large arc on the plane including the crotch and counter-crotch side lines has a length equal to an addition of a difference between the radius of the reference arc on the plane including the crotch and counter-crotch side lines passing through the reference point in the lateral direction and the radius of said small arc on the plane including the crotch and counter-crotch side lines to the radius of the reference arc on the plane including the crotch and counter-crotch side lines, and the radius of said large arc on the plane including the anterior and posterior side lines has a length equal to an addition of a difference between the radius of the reference arc on the plane including the anterior and posterior side line passing through the reference point in a direction perpendicular to a lateral direction and the radius of said small arc on the plane including the anterior and posterior side line to the radius of the reference arc on the plane including the anterior and posterior side lines.

5. The method of determining the shape of an artificial cement-less hip prosthesis stem according to claim 2, wherein:

a ratio of a distance from said straight segment to the alternative reference point in the lateral direction taken between said straight segment and said reference point in the lateral direction to the distance from the straight segment to said reference point in the lateral direction, is defined by a bending ratio α on a plane along the lateral direction, and a ratio of a distance from the straight segment to the alternative reference point in a direction perpendicular to the lateral direction taken between said straight segment and said reference point in the direction perpendicular to the lateral direction to the distance from the straight segment to said reference point in the direction perpendicular to the lateral direction, is defined by a bending ratio β on a plane along a direction perpendicular to the lateral direction, wherein in one or more of the following cases where α=0 and β=0
α=0.5 and β=0
α=1 and β=0
α=0 and β=0.5
α=0.5 and β=0.5
α=1 and β=0.5
α=0 and β=1
α=0.5 and β=1
α=1 and β=1 transitional values of positions and postures of imaginary rasps given a same shape and size as the reference stem and the alternative stem having said final shape, are calculated while the imaginary rasps are independently pushed step by step into the imaginary three dimensional deep hollow.

6. The method of determining the shape of an artificial cement-less hip prosthesis stem according to claim 5, wherein:

after obtaining said cases where the imaginary rasps are pushed into the imaginary three dimensional deep hollow, the bending ratio a on the plane along the lateral direction and the bending ratio β on the plane along the direction perpendicular to the lateral direction can be changed into desired values, a final shape of a re-alternative stem corresponding to said reference stem is obtained by regarding a re-alternative reference point in the lateral direction obtained from a new ratio a as said reference point in the lateral direction, and by regarding a re-alternative reference point in the direction perpendicular to the lateral direction obtained from the new ratio β as said reference point in the direction perpendicular to the lateral direction, data on positions and postures of the re-alternative stem having the final shape are computed for every step while putting the re-alternative stem into said imaginary three dimensional deep hollow, by reversing the series of method steps, and transitional values of positions and postures of a re-imaginary rasp having a same shape and size as a re-alternative stem having a final shape are computed while putting the re-alternative rasp step by step into the imaginary deep hollow.

7. The method of determining the shape of an artificial cement-less hip prosthesis stem according to claim 6, further comprising:

after pushing said reference stem, the alternative stem and the re-alternative stem into said imaginary three dimensional deep hollow, calculating rates of fit and fill for each section of the stem along said reference line.

8. The method of determining the shape of an artificial cement-less hip prosthesis stem according to claim 1, wherein:

the radius of said small arc on the plane including the crotch and counter-crotch side lines is equal to a radius of a pseudo-arc regarded as the crotch side line which passes through the end point of the diaphysis and the end point of the epiphysis lying on the crotch side line of said imaginary three dimensional deep hollow, and a point most protruded in a lateral direction on the crotch side line, where a line parallel to a straight line passing through these two end points contacts the crotch side line, and the radius of said small arc on the plane including the anterior and posterior side lines is equal to a radius of a pseudo-arc regarded as the anterior side line which passes through the end point of the diaphysis and the end point of the epiphysis lying on the anterior side line of said imaginary three dimensional deep hollow, and a point most protruded in a direction perpendicular to the lateral direction on the anterior side line, where a line parallel to a straight line passing through these two end points contacts the anterior side line.

9. The method of determining the shape of an artificial cement-less hip prosthesis stem according to claim 8, wherein:

the radius of said large arc on the plane including the crotch and counter-crotch side lines has a length equal to an addition of a difference between the radius of the reference arc on the plane including the crotch and counter-crotch side lines passing through the reference point in the lateral direction and the radius of said small arc on the plane including the crotch and counter-crotch side lines to the radius of the reference arc on the plane including the crotch and counter-crotch side lines, and the radius of said large arc on the plane including the anterior and posterior side lines has a length equal to an addition of a difference between the radius of the reference arc on the plane including the anterior and posterior side line passing through the reference point in a direction perpendicular to a lateral direction and the radius of said small arc on the plane including the anterior and posterior side line to the radius of the reference arc on the plane including the anterior and posterior side lines.

10. The method of determining the shape of an artificial cement-less hip prosthesis stem according to claim 8, wherein:

a ratio of a distance from said straight segment to the alternative reference point in the lateral direction taken between said straight segment and said reference point in the lateral direction to the distance from the straight segment to said reference point in the lateral direction, is defined by a bending ratio α on a plane along the lateral direction, and a ratio of a distance from the straight segment to the alternative reference point in a direction perpendicular to the lateral direction taken between said straight segment and said reference point in the direction perpendicular to the lateral direction to the distance from the straight segment to said reference point in the direction perpendicular to the lateral direction, is defined by a bending ratio β on a plane along a direction perpendicular to the lateral direction, wherein in one or more of the following cases where α=0 and β=0
α=0.5 and β=0
α=1 and β=0
α=0 and β=0.5
α=0.5 and β=0.5
α=1 and β=0.5
α=0 and β=1
α=0.5 and β=1
α=1 and β=1 transitional values of positions and postures of imaginary rasps given a same shape and size as the reference stem and the alternative stem having said final shape, are calculated while the imaginary rasps are independently pushed step by step into the imaginary three dimensional deep hollow.

11. The method of determining the shape of an artificial cement-less hip prosthesis stem according to claim 10, wherein:

after obtaining said cases where the imaginary rasps are pushed into the imaginary three dimensional deep hollow, the bending ratio α on the plane along the lateral direction and the bending ratio β on the plane along the direction perpendicular to the lateral direction can be changed into desired values, a final shape of a re-alternative stem corresponding to said reference stem is obtained by regarding a re-alternative reference point in the lateral direction obtained from a new ratio a as said reference point in the lateral direction, and by regarding a re-alternative reference point in the direction perpendicular to the lateral direction obtained from the new ratio β as said reference point in the direction perpendicular to the lateral direction, data on positions and postures of the re-alternative stem having the final shape are computed for every step while putting the re-alternative stem into said imaginary three dimensional deep hollow, by reversing the series of method steps, and transitional values of positions and postures of a re-imaginary rasp having a same shape and size as a re-alternative stem having a final shape are computed while putting the re-alternative rasp step by step into the imaginary deep hollow.

12. The method of determining the shape of an artificial cement-less hip prosthesis stem according to claim 11, further comprising:

after pushing said reference stem, the alternative stem and the re-alternative stem into said imaginary three dimensional deep hollow, calculating rates of fit and fill for each section of the stem along said reference line.

13. The method of determining the shape of an artificial cement-less hip prosthesis stem according to claim 1, wherein:

the radius of said large arc on the plane including the crotch and counter-crotch side lines has a length equal to an addition of a difference between the radius of the reference arc on the plane including the crotch and counter-crotch side lines passing through the reference point in the lateral direction and the radius of said small arc on the plane including the crotch and counter-crotch side lines to the radius of the reference arc on the plane including the crotch and counter-crotch side lines, and the radius of said large arc on the plane including the anterior and posterior side lines has a length equal to an addition of a difference between the radius of the reference arc on the plane including the anterior and posterior side line passing through the reference point in a direction perpendicular to a lateral direction and the radius of said small arc on the plane including the anterior and posterior side line to the radius of the reference arc on the plane including the anterior and posterior side lines.

14. The method of determining the shape of an artificial cement-less hip prosthesis stem according to claim 13, wherein:

said reference point in the lateral direction is a midpoint of a line from the point most protruded in the lateral direction on the crotch side line to a cross point where the line passing through the center of said pseudo-arc is regarded as the crotch side line and the point most protruded in the lateral direction on the crotch side line intersects the counter-crotch side line, said reference point in the direction perpendicular to the lateral direction is a midpoint of a line from the point most protruded in the direction perpendicular to the lateral direction on the anterior side line to a cross point where the line passing through the center of said pseudo-arc is regarded as the anterior side line and the point most protruded in the direction perpendicular to the lateral direction on the anterior side line intersects the posterior side line.

15. The method of determining the shape of an artificial cement-less hip prosthesis stem according to claim 14, wherein:

a ratio of a distance from said straight segment to the alternative reference point in the lateral direction taken between said straight segment and said reference point in the lateral direction to the distance from the straight segment to said reference point in the lateral direction, is defined by a bending ratio α on a plane along the lateral direction, and a ratio of a distance from the straight segment to the alternative reference point in a direction perpendicular to the lateral direction taken between said straight segment and said reference point in the direction perpendicular to the lateral direction to the distance from the straight segment to said reference point in the direction perpendicular to the lateral direction, is defined by a bending ratio β on a plane along a direction perpendicular to the lateral direction, wherein in one or more of the following cases where α=0 and β=0
α=0.5 and β=0
α=1 and β=0
α=0 and β=0.5
α=0.5 and β=0.5
α=1 and β=0.5
α=0 and β=1
α=0.5 and β=1
α=1 and β=1 transitional values of positions and postures of imaginary rasps given a same shape and size as the reference stem and the alternative stem having said final shape, are calculated while the imaginary rasps are independently pushed step by step into the imaginary three dimensional deep hollow.

16. The method of determining the shape of an artificial cement-less hip prosthesis stem according to claim 15, wherein:

after obtaining said cases where the imaginary rasps are pushed into the imaginary three dimensional deep hollow, the bending ratio α on the plane along the lateral direction and the bending ratio β on the plane along the direction perpendicular to the lateral direction can be changed into desired values, a final shape of a re-alternative stem corresponding to said reference stem is obtained by regarding a re-alternative reference point in the lateral direction obtained from a new ratio α as said reference point in the lateral direction, and by regarding a re-alternative reference point in the direction perpendicular to the lateral direction obtained from the new ratio β as said reference point in the direction perpendicular to the lateral direction, data on positions and postures of the re-alternative stem having the final shape are computed for every step while putting the re-alternative stem into said imaginary three dimensional deep hollow, by reversing the series of method steps, and transitional values of positions and postures of a re-imaginary rasp having a same shape and size as a re-alternative stem having a final shape are computed while putting the re-alternative rasp step by step into the imaginary deep hollow.

17. The method of determining the shape of an artificial cement-less hip prosthesis stem according to claim 16, further comprising:
after pushing said reference stem, the alternative stem and the re-alternative stem into said imaginary three dimensional deep hollow, calculating rates of fit and fill for each section of the stem along said reference line.

18. The method of determining the shape of an artificial cement-less hip prosthesis stem according to claim 13, wherein:
a ratio of a distance from said straight segment to the alternative reference point in the lateral direction taken between said straight segment and said reference point in the lateral direction to the distance from the straight segment to said reference point in the lateral direction, is defined by a bending ratio $\alpha$ on a plane along the lateral direction, and a ratio of a distance from the straight segment to the alternative reference point in a direction perpendicular to the lateral direction taken between said straight segment and said reference point in the direction perpendicular to the lateral direction to the distance from the straight segment to said reference point in the direction perpendicular to the lateral direction, is defined by a bending ratio $\beta$ on a plane along a direction perpendicular to the lateral direction, wherein in one or more of the following cases where
$\alpha=0$ and $\beta=0$
$\alpha=0.5$ and $\beta=0$
$\alpha=1$ and $\beta=0$
$\alpha=0$ and $\beta=0.5$
$\alpha=0.5$ and $\beta=0.5$
$\alpha=1$ and $\beta=0.5$
$\alpha=0$ and $\beta=1$
$\alpha=0.5$ and $\beta=1$
$\alpha=1$ and $\beta=1$
transitional values of positions and postures of imaginary rasps given a same shape and size as the reference stem and the alternative stem having said final shape, are calculated while the imaginary rasps are independently pushed step by step into the imaginary three dimensional deep hollow.

19. The method of determining the shape of an artificial cement-less hip prosthesis stem according to claim 18, wherein:
after obtaining said cases where the imaginary rasps are pushed into the imaginary three dimensional deep hollow, the bending ratio $\alpha$ on the plane along the lateral direction and the bending ratio $\beta$ on the plane along the direction perpendicular to the lateral direction can be changed into desired values,
a final shape of a re-alternative stem corresponding to said reference stem is obtained by regarding a re-alternative reference point in the lateral direction obtained from a new ratio $\alpha$ as said reference point in the lateral direction, and by regarding a re-alternative reference point in the direction perpendicular to the lateral direction obtained from the new ratio $\beta$ as said reference point in the direction perpendicular to the lateral direction,
data on positions and postures of the re-alternative stem having the final shape are computed for every step while putting the re-alternative stem into said imaginary three dimensional deep hollow, by reversing the series of method steps, and transitional values of positions and postures of a re-imaginary rasp having a same shape and size as a re-alternative stem having a final shape are computed while putting the re-alternative rasp step by step into the imaginary deep hollow.

20. The method of determining the shape of an artificial cement-less hip prosthesis stem according to claim 19, further comprising:
after pushing said reference stem, the alternative stem and the re-alternative stem into said imaginary three dimensional deep hollow, calculating rates of fit and fill for each section of the stem along said reference line.

21. The method of determining the shape of an artificial cement-less hip prosthesis stem according to claim 1, wherein:
a ratio of a distance from said straight segment to the alternative reference point in the lateral direction taken between said straight segment and said reference point in the lateral direction to the distance from the straight segment to said reference point in the lateral direction, is defined by a bending ratio $\alpha$ on a plane along the lateral direction, and a ratio of a distance from the straight segment to the alternative reference point in a direction perpendicular to the lateral direction taken between said straight segment and said reference point in the direction perpendicular to the lateral direction to the distance from the straight segment to said reference point in the direction perpendicular to the lateral direction, is defined by a bending ratio $\beta$ on a plane along a direction perpendicular to the lateral direction, wherein in one or more of the following cases where
$\alpha=0$ and $\beta=0$
$\alpha=0.5$ and $\beta=0$
$\alpha=1$ and $\beta=0$
$\alpha=0$ and $\beta=0.5$
$\alpha=0.5$ and $\beta=0.5$
$\alpha=1$ and $\beta=0.5$
$\alpha=0$ and $\beta=1$
$\alpha=0.5$ and $\beta=1$
$\alpha=1$ and $\beta=1$
transitional values of positions and postures of imaginary rasps, given a same shape and size as the reference stem and the alternative stem having said final shape, are calculated while the imaginary rasps are independently pushed step by step into the imaginary three dimensional deep hollow.

22. The method of determining the shape of an artificial cement-less hip prosthesis stem according to claim 21, wherein:
after obtaining said cases where the imaginary rasps are pushed into the imaginary three dimensional deep hollow, the bending ratio a on the plane along the lateral direction and the bending ratio $\beta$ on the plane along the direction perpendicular to the lateral direction are changeable into desired values,
a final shape of a re-alternative stem corresponding to said reference stem is obtained by regarding a re-alternative reference point in the lateral direction obtained from a new ratio $\alpha$ as said reference point in the lateral direction, and by regarding a re-alternative reference point in the direction perpendicular to the lateral direction obtained from the new ratio $\beta$ as said reference point in the direction perpendicular to the lateral direction,
computing data on positions and postures of the re-alternative stem having the final shape for every step while putting the re-alternative stem into said imaginary three dimensional deep hollow, and computing transitional values of positions and postures of a re-imaginary rasp having a same shape and size as a re-alternative stem having a final shape while putting the re-alternative rasp step by step into the imaginary deep hollow.

23. The method of determining the shape of an artificial cement-less hip prosthesis stem according to claim 22, further comprising:

after pushing said reference stem, the alternative stem and the re-alternative stem into said imaginary three dimensional deep hollow, calculating rates of fit and fill for each section of the stem along said reference line.

* * * * *